United States Patent
Jagasia et al.

(10) Patent No.: US 9,670,206 B2
(45) Date of Patent: Jun. 6, 2017

(54) PYRIDO[4,3-B]PYRAZINE-2-CARBOXAMIDES AS NEUROGENIC AGENTS FOR THE TREATMENT OF NEURODEGENERATIVE DISORDERS

(71) Applicant: Hoffmann-La Roche Inc., Little Falls, NJ (US)

(72) Inventors: Ravi Jagasia, Loerrach (DE); Roland Jakob-Roetne, Inzlingen (DE); Jens-Uwe Peters, Grenzach-Wyhlen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 36 days.

(21) Appl. No.: 15/151,698

(22) Filed: May 11, 2016

(65) Prior Publication Data
US 2016/0251355 A1     Sep. 1, 2016

Related U.S. Application Data

(63) Continuation of application No. PCT/EP2014/073988, filed on Nov. 7, 2014.

(30) Foreign Application Priority Data

Nov. 13, 2013 (EP) .................................... 13192406

(51) Int. Cl.
| | |
|---|---|
| C07D 471/04 | (2006.01) |
| A61K 31/4985 | (2006.01) |
| A61P 25/18 | (2006.01) |
| A61P 25/24 | (2006.01) |
| A61P 25/22 | (2006.01) |

(52) U.S. Cl.
CPC .................. *C07D 471/04* (2013.01)

(58) Field of Classification Search
None
See application file for complete search history.

(56) References Cited

FOREIGN PATENT DOCUMENTS

| | | |
|---|---|---|
| CN | 102414180 A | 11/2012 |
| WO | WO 2010/101949 A1 | 10/2010 |
| WO | W2012/006419 A2 * | 1/2012 |

* cited by examiner

*Primary Examiner* — Timothy R Rozof

(57) ABSTRACT

The present invention relates to compounds of general formula I wherein $R^1$, $R^2$ and $R^3$ are as defined herein which may be used for the treatment of schizophrenia, obsessive-compulsive

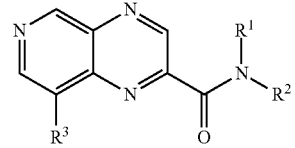

personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuroactive drugs, selected from alcohol, opiates, methamphetamine, phencyclidine and cocaine.

8 Claims, No Drawings

PYRIDO[4,3-B]PYRAZINE-2-CARBOXAMIDES AS NEUROGENIC AGENTS FOR THE TREATMENT OF NEURODEGENERATIVE DISORDERS

CROSS REFERENCE TO RELATED APPLICATIONS

This application is a continuation of International Application No. PCT/EP2014/073988 having an international filing date of Nov. 7, 2014 and which claims benefit under 35 U.S.C. §119 to European Patent Application No. 13192406.0 filed Nov. 12, 2013. The entire contents of both are incorporated herein by reference.

FIELD OF THE INVENTION

The present invention relates to novel compounds of formula I, wherein $R^1$, $R^2$, $R^3$, and $R^4$ are as described herein, having pharmaceutical activity, their manufacture, pharmaceutical compositions containing them and their potential use as medicaments.

BACKGROUND OF THE INVENTION

Neurogenesis occurs in the developing and adult brain. Conceptually, the process of neurogenesis can be divided into four steps: (i) proliferation of neural stem cells (NSCs); (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyrus of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyrus, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

The stimulation of adult neurogenesis represents also a therapeutic target for optic neuropathy (S. Isenmann, A. Kretz, A. Cellerino, Progress in Retinal and Eye Research, 22, (2003) 483) and macular degeneration (G. Landa, O. Butovsky, J. Shoshani, M. Schwartz, A. Pollack, Current Eye Research 33, (2008) 1011).

Hence, chemical stimulation of adult neurogenesis offers new regenerative avenues and opportunities to develop novel drugs for treating neurological diseases and neuropsychiatric disorders.

Compounds that modulate neurogenesis may therefore be useful for treating of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine and cocaine.

The most preferred indications for compounds of formula I are Alzheimer's disease, depression, anxiety disorders and stroke.

BRIEF SUMMARY OF THE INVENTION

The present invention relates to compounds of general formula

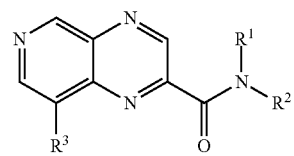

(I)

wherein
$R^1$ is hydrogen;

R² is hydrogen, lower alkyl, benzyl, lower alkyl substituted by hydroxy or is cycloalkyl optionally substituted by cyano;

or R¹ and R² form together with the N-atom to which they are attached a heterocycloalkyl group, optionally containing an additional N, O or S ring atom, and which is optionally substituted by hydroxy;

R³ is halogen, phenyl optionally substituted by one or more halogen, cyano, lower alkyl substituted by halogen, lower alkoxy substituted by halogen or by lower alkyl substituted by hydroxy, or is heteroaryl, optionally substituted by lower alkyl or halogen, or is 3,6-dihydro-pyran-4-yl, or is piperidin-1-yl optionally substituted by one or more halogen;

or to a pharmaceutically acceptable acid addition salt, to a racemic mixture or to its corresponding enantiomer and/or optical isomer thereof.

Another object of the invention are pharmaceutical compositions, containing a compound of formula I.

Yet another object of the present invention is the use of a compound of formula I for the preparation of medicaments for the therapeutic and/or prophylactic treatment of the above-mentioned diseases.

A further object of the invention is a method for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, optic neuropathy or macular degeneration, abuse of neuro-active drugs, such as alcohol, opiates, methamphetamine, phencyclidine and cocaine, which method comprises administering an effective amount of a compound of formula I.

DETAILED DESCRIPTION OF THE INVENTION

The present invention relates to compounds of formula I and to their pharmaceutically acceptable salts, in cases where this applies to mixtures of enantiomers or diastereomers or their enantiomerically or diastereomerically pure forms, to these compounds as pharmaceutically active substances, to the processes for their production, as well as to the use in the treatment or prevention of disorders, relating to neurogenesis, schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine.

One embodiment of the present invention is to provide compounds of Formula I wherein R¹, R², R³ and R⁴ are as defined in the Brief Summary of the Invention.

Another embodiment of the invention are compounds of formula I, wherein R¹ is hydrogen, R² is hydrogen, lower alkyl, benzyl, lower alkyl substituted by hydroxy or cycloalkyl optionally substituted by cyano, and R³ is as described in the Brief Summary of the Invention.

Another embodiment of the present invention is a compound selected from:

8-(4-Chlorophenyl)pyrido[4,3-b]pyrazine-2-carboxamide 8-(4-(Trifluoromethyl)phenyl)pyrido[4,3-b]pyrazine-2-carboxamide 8-Bromo-N-(1-cyanocyclopropyl)pyrido[4,3-b]pyrazine-2-carboxamide 8-(4-Chlorophenyl)-N-(3-hydroxy-3-methylbutan-2-yl)pyrido[4,3-b]pyrazine-2-carboxamide N-(3-Hydroxy-3-methylbutan-2-yl)-8-(4-(trifluoromethyl)phenyl)pyrido[4,3-b]pyrazine-2-carboxamide 8-(4-Chlorophenyl)-N-(1-cyanocyclopropyl)pyrido[4,3-b]pyrazine-2-carboxamide N-(1-Cyanocyclopropyl)-8-(4-(trifluoromethyl)phenyl)pyrido[4,3-b]pyrazine-2-carboxamide N-Benzyl-8-(4-(trifluoromethyl)phenyl)pyrido[4,3-b]pyrazine-2-carboxamide N-Benzyl-8-(4-chlorophenyl)pyrido[4,3-b]pyrazine-2-carboxamide 8-(2,4-Dichlorophenyl)pyrido[4,3-b]pyrazine-2-carboxamide 8-(4-Fluorophenyl)pyrido[4,3-b]pyrazine-2-carboxamide 8-(3,4,5-Trifluorophenyl)pyrido[4,3-b]pyrazine-2-carboxamide 8-(2-Fluorophenyl)pyrido[4,3-b]pyrazine-2-carboxamide 8-(2-Fluoro-4-(trifluoromethyl)phenyl)pyrido[4,3-b]pyrazine-2-carboxamide 8-(6-Chloropyridin-3-yl)pyrido[4,3-b]pyrazine-2-carboxamide 8-(4-(Trifluoromethoxy)phenyl)pyrido[4,3-b]pyrazine-2-carboxamide 8-(2-Fluoro-5-(trifluoromethyl)phenyl)pyrido[4,3-b]pyrazine-2-carboxamide 8-(3-(Trifluoromethoxy)phenyl)pyrido[4,3-b]pyrazine-2-carboxamide 8-(4-Chloro-2-fluorophenyl)pyrido[4,3-b]pyrazine-2-carboxamide 8-(4-Chloro-3-fluorophenyl)pyrido[4,3-b]pyrazine-2-carboxamide 8-(3-Fluoro-4-(trifluoromethyl)phenyl)pyrido[4,3-b]pyrazine-2-carboxamide 8-(3,6-Dihydro-2H-pyran-4-yl)pyrido[4,3-b]pyrazine-2-carboxamide 8-(3-(Trifluoromethyl)phenyl)pyrido[4,3-b]pyrazine-2-carboxamide 8-(3,4-Difluorophenyl)pyrido[4,3-b]pyrazine-2-carboxamide 8-(4-(Hydroxymethyl)phenyl)pyrido[4,3-b]pyrazine-2-carboxamide N-Benzyl-8-(pyridin-3-yl)pyrido[4,3-b]pyrazine-2-carboxamide 8-(4-Cyanophenyl)pyrido[4,3-b]pyrazine-2-carboxamide N-tert-Butyl-8-(4-(trifluoromethyl)phenyl)pyrido[4,3-b]pyrazine-2-carboxamide 8-(2,4-Dichlorophenyl)-N-(3-hydroxy-3-methylbutan-2-yl)pyrido[4,3-b]pyrazine-2-carboxamide 8-(2-Chlorophenyl)-N-(3-hydroxy-3-methylbutan-2-yl)pyrido[4,3-b]pyrazine-2-carboxamide 8-(4,4-Difluoropiperidin-1-yl)pyrido[4,3-b]pyrazine-2-carboxamide
8-(4-Chloro-3-fluorophenyl)-N-(3-hydroxy-3-methylbutan-2-yl)pyrido[4,3-b]pyrazine-2-carboxamide
N-(3-Hydroxy-3-methylbutan-2-yl)-8-(3,4,5-trifluorophenyl)pyrido[4,3-b]pyrazine-2-carboxamide
N-(3-Hydroxy-3-methylbutan-2-yl)-8-(1-methyl-1H-pyrazol-5-yl)pyrido[4,3-b]pyrazine-2-carboxamide
8-(1-Methyl-1H-pyrazol-5-yl)pyrido[4,3-b]pyrazine-2-carboxamide
N-(3-Hydroxy-3-methylbutan-2-yl)-8-(6-methylpyridin-3-yl)pyrido[4,3-b]pyrazine-2-carboxamide, or
N-(3-Hydroxy-3-methylbutan-2-yl)-8-(6-methylpyridin-2-yl)pyrido[4,3-b]pyrazine-2-carboxamide,
or a pharmaceutically acceptable acid addition salt, to a racemic mixture or to it corresponding enantiomer and/or optical isomer thereof.

Another embodiment of the invention are compounds of formula I, wherein $R^1$ and $R^2$ form together with the N-atom to which they are attached a heterocycloalkyl group, optionally containing an additional N, O or S ring atom, and which is optionally substituted by hydroxy, and $R^3$ is as described in the Brief Summary of the Invention.

Another embodiment of the present invention is a compound selected from:
(8-Bromopyrido[4,3-b]pyrazin-2-yl)(morpholino)methanone
(8-(4-Chlorophenyl)pyrido[4,3-b]pyrazin-2-yl)(morpholino)methanone
Morpholino(8-(4-(trifluoromethyl)phenyl)pyrido[4,3-b]pyrazin-2-yl)methanone
(3-Hydroxypyrrolidin-1-yl)(8-(4-(trifluoromethyl)phenyl)pyrido[4,3-b]pyrazin-2-yl)methanone
(8-(4-Chlorophenyl)pyrido[4,3-b]pyrazin-2-yl)(3-hydroxypyrrolidin-1-yl)methanone
[8-(4-Chlorophenyl)pyrido[3,4-b]pyrazin-2-yl]-(1,1-dioxo-1,4-thiazinan-4-yl)methanone
(1,1-Dioxo-1,4-thiazinan-4-yl)-[8-[4-(trifluoromethyl)phenyl]pyrido[3,4-b]pyrazin-2-yl]methanone
(8-(4-Chloro-2-fluorophenyl)pyrido[4,3-b]pyrazin-2-yl)(3-hydroxypyrrolidin-1-yl)methanone
8-(2,4-Dichlorophenyl)pyrido[4,3-b]pyrazin-2-yl)(3-hydroxypyrrolidin-1-yl)methanone
(8-(2-Fluoro-5-(trifluoromethyl)phenyl)pyrido[4,3-b]pyrazin-2-yl)(3-hydroxypyrrolidin-1-yl)methanone
(3-Hydroxypyrrolidin-1-yl)(8-(3-(trifluoromethoxy)phenyl)pyrido[4,3-b]pyrazin-2-yl)methanone
(8-(6-Chloropyridin-3-yl)pyrido[4,3-b]pyrazin-2-yl)(3-hydroxypyrrolidin-1-yl)methanone
(8-(4-Chloro-3-fluorophenyl)pyrido[4,3-b]pyrazin-2-yl)(3-hydroxypyrrolidin-1-yl)methanone
(8-(2-Fluoro-4-(trifluoromethyl)phenyl)pyrido[4,3-b]pyrazin-2-yl)(3-hydroxypyrrolidin-1-yl)methanone
(8-(4-(Hydroxymethyl)phenyl)pyrido[4,3-b]pyrazin-2-yl)(3-hydroxypyrrolidin-1-yl)methanone, or,
(8-(3-Fluoro-4-(trifluoromethyl)phenyl)pyrido[4,3-b]pyrazin-2-yl)(3-hydroxypyrrolidin-1-yl)methanone,
or a pharmaceutically acceptable acid addition salt, to a racemic mixture or to it corresponding enantiomer and/or optical isomer thereof.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, and isopropyl.

The term "alkoxy" denotes a group —O—R' wherein R' is lower alkyl as defined above.

The term "lower alkyl substituted by halogen" denotes a lower alkyl group as defined above, wherein at least one hydrogen atom is replaced by a halogen atom. The preferred group is $CF_3$.

The term "lower alkoxy substituted by halogen" denotes a lower alkoxy group as defined above, wherein at least one hydrogen atom is replaced by a halogen atom. The preferred group is $OCF_3$.

The term "lower alkyl substituted by hydroxy" denotes a lower alkyl group as defined above, wherein at least one hydrogen atom is replaced by a hydroxy group. The preferred group is $CH(CH_3)C(OH)(CH_3)_2$.

The term "cycloalkyl" denotes a carbon ring with 3-7 carbon atoms.

The term "heterocycloalkyl" comprises non aromatic rings, containing at least one heteroatom, selected from N, O or S. Such groups are piperidinyl, morpholinyl, pyrrolidinyl, piperazinyl or 1,1-di-oxo-thiomprpholinyl.

The term "heteroaryl" denotes a carbocyclic ring system, containing from 5 to 10 ring atoms forming one or more rings, wherein at least one carbon atom is replaced by a heteroatom, selected from the group consisting of O, N or S, and wherein at least one ring is aromatic in nature, for example oxazolyl, pyridyl, thiophenyl, quinolinyl, pyrrolyl, furyl, benzoimidazolyl, imidazolyl, pyrazoyl and the like. The most preferred groups are pyridyl and pyrazolyl The term "halogen" denotes chlorine, bromine, fluorine or iodine.

The present new compounds of formula I and their pharmaceutically acceptable salts can be prepared by methods known in the art, for example, by processes described below, which process comprises a) reacting a compound of formula 4

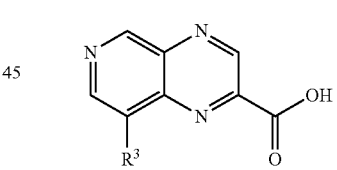

with a compound of formula 2

to a compound of formula I

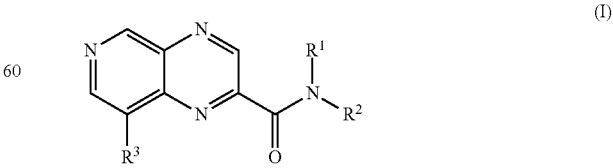

and, if desired, converting the compounds obtained into pharmaceutically acceptable acid addition salts, or b) reacting a compound of formula I-1

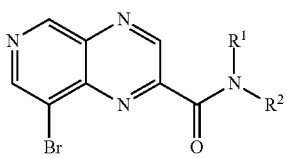

with a compound of formula 3

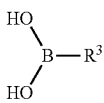

to a compound of formula I

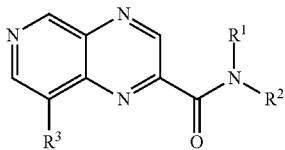

and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

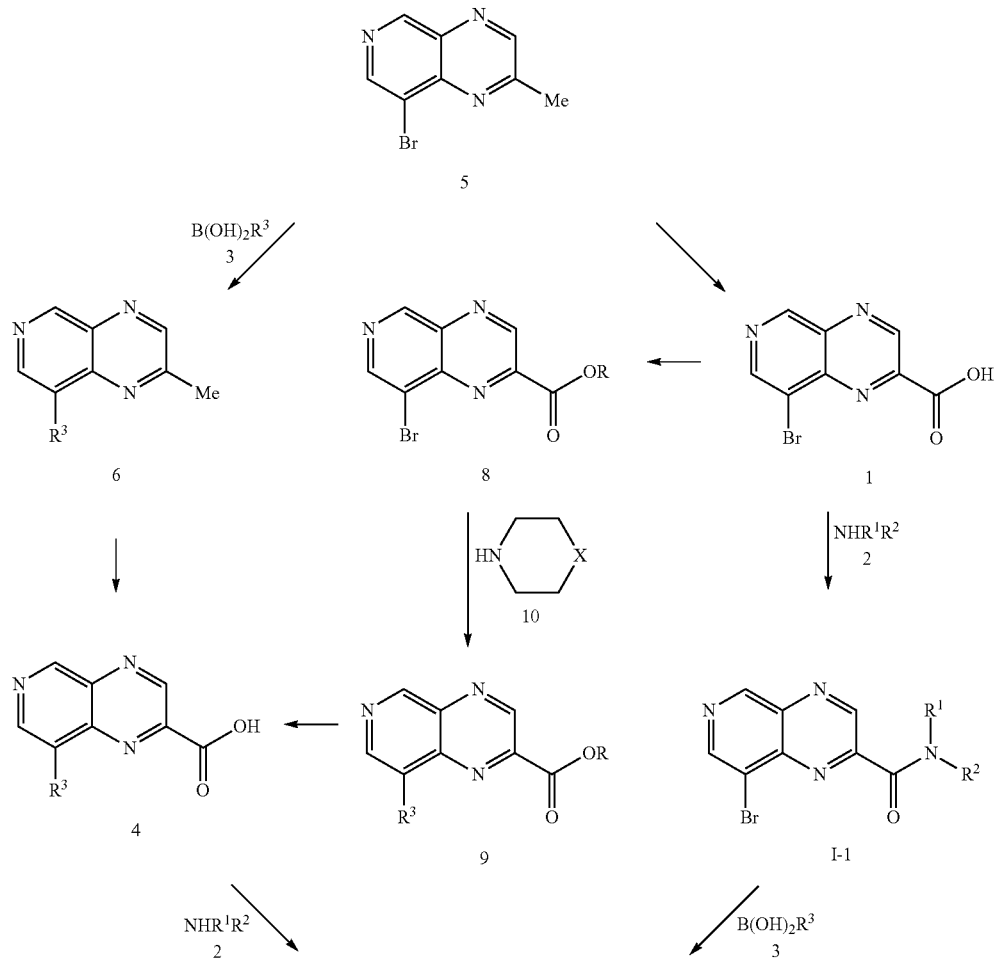

Scheme 1

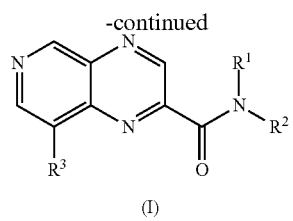

(I)

The precursor compounds of formula 4 can be prepared by methods known in the art.

To a suspension of 8-bromo-2-methyl-pyrido[3,4-b]pyrazine (formula 5) and a boronic acid of formula 3 and cesium carbonate in dioxane and water is added bis(diphenylphosphino)ferrocene-palladium(II)dichloride. The mixture is stirred at 80° C. for 3 hours. Removal of the solvent by distillation and chromatography yields the compound of formula 6.

Furthermore, the 8-substituted 2-methylpyrido[4,3-b]pyrazine of formula 6 was combined with selenium dioxide in dioxane and was heated at 100° C. for 3 hours. The resulting aldehyde was combined with t-butanol, 2-methylbut-2-ene, sodium chlorite and sodium dihydrogen phosphate in water and was stirred at room temperature overnight to yield a compound of formula 4.

Furthermore, the oxidation of 8-bromo-2-methyl-pyrido[3,4-b]pyrazine (formula 5) for example with selenium dioxide followed by sodium chlorite oxidation to result in the formation of 8-bromo-pyrido[3,4b]pyrazine-2-carboxylic acid (formula 1), followed by esterification to a compound of formula 8, which is then reacted with a compound of formula 10 (X=CF$_2$) to a compound of formula 9 and ester cleavage results in the formation of a compound of formula 4.

In more detail, a mixture of 8-bromo-2-methylpyrido[4,3-b]pyrazine (formula 5) with selenium dioxide in dioxane and was heated at 100° C. for 3 hours. The resulting aldehyde was combined with t-butanol, 2-methylbut-2-ene, sodium chlorite and sodium dihydrogen phosphate in water and was stirred at room temperature 2 days to yield 8-bromo-pyrido[3,4-b]pyrazine-2-carboxylic acid (formula 1).

A mixture of 8-bromo-pyrido[3,4-b]pyrazine-2-carboxylic acid of formula 1, N, N-diisopropylethylamine and O-(7-azabenzotriazol-1-yl)-N,N,N',N'-tetramethyluronium hexafluorophosphate (HATU) in dimethylformamide is stirred at room temperature for 10 minutes. The corresponding amine of formula 2 is added and stirring is continued over overnight to yield a compound of formula I-1.

Furthermore, to a suspension of 8-bromo-pyrido[3,4-b]pyrazine-2-carboxylic acid amide of formula I-1 and a boronic acid of formula 3 and cesium carbonate in dioxane and water is added bis(diphenylphosphino)ferrocene-palladium(II)dichloride. The mixture is stirred at 80° C. for 3 hours. Removal of the solvent by distillation and chromatography yields the compound of formula I.

Or, a mixture of 8-(4-chlorophenyl)pyrido[4,3-b]pyrazine-2-carboxylic acid of formula 4 and 1,1'-carbonyldiimidazole in dichloromethane was combined with the corresponding amine of formula 2. The mixture was stirred at room temperature overnight to yield a compound of formula I.

A mixture of 8-bromopyrido[4,3-b]pyrazine-2-carboxylic acid (formula 1) and oxalyl chloride in dichloromethane was stirred at 0° C. for 1 hour and then at room temperature for 1 hour. The mixture was concentrated in vacuo and dissolved in dichloromethane. Methanol was added and the mixture was concentrated in vacuo to yield methyl-8-bromopyrido[4,3-b]pyrazine-2-carboxylate (formula 8).

A suspension of 8-bromopyrido[4,3-b]pyrazine-2-carboxylate (formula 8) and cesium carbonate in toluene (6.0 ml) was combined with palladium(II)acetate and 2,2'-bis(diphenylphosphino)-1,1'-binaphthyl (BINAP) and 4,4-difluoropiperidine. The reaction mixture was heated at 80° C. for 5 hours. Purification by chromatography yields the compound of formula 9.

A solution of methyl 8-(4,4-difluoropiperidin-1-yl)pyrido[4,3-b]pyrazine-2-carboxylate (compound of formula 9) in dioxane and water was treated with aqueous lithium hydroxide. Acidification and extraction yields the compound of formula 4.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)
Compounds respond is measured by the increase in cells based on ATP levels (Promega:CellTiterGlo®) after an incubation period of 4 days.
NSCs are thawed and expanded over 3 passages. On the 14$^{th}$ day, NSCs are seeded in Polyornithin/Laminin coated 384 well plates at a cell density of 21,000 cells/cm$^2$ in a media volume of 38 μl.
4 hours after cell seeding, compound solutions are added at a volume of 2 μl. Stock solutions of the compounds (water, 5% DMSO) are diluted to obtain a dose response (11 points, dilution factor is 2), ranging from 8 μM to 8 nM. Controls are run to consistently determine the neurogenic properties of the cells:

Negative (neutral) control is cell culture Media (final DMSO concentration: 0.25%). Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.
The value of negative (neutral) control is determined for each assay plate by taking the average of 16 negative control wells. The neurogenic compound response is calculated for each compound as (compound/Negative Control)*100.
The values of $EC_{150}$ from the dose response curve are determined for each test compound. The EC150 is the compound concentration at which 150% activity of control (100%) is reached. The preferred compounds show a $EC_{150}$ (μM) in the range of <3.0 μM as shown in Table 1.

TABLE 1

List of examples and $EC_{150}$ data

| Example | Structure | Name | $EC_{150}$ (uM) |
|---|---|---|---|
| 1 | 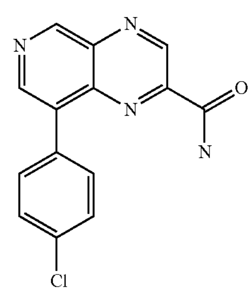 [SMILES: NC(=O)c1cnc2cncc(-c3ccc(Cl)cc3)c2n1] | 8-(4-Chlorophenyl)pyrido[4,3-b]pyrazine-2-carboxamide | 0.21 |
| 2 | 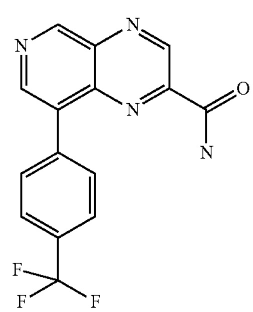 [SMILES: NC(=O)c1cnc2cncc(-c3ccc(C(F)(F)F)cc3)c2n1] | 8-(4-(Trifluoromethyl)phenyl)pyrido[4,3-b]pyrazine-2-carboxamide | 0.30 |
| 3 | 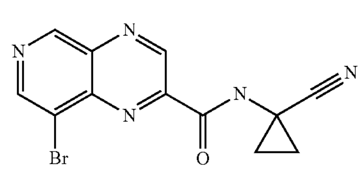 [SMILES: N#CC1(NC(=O)c2cnc3cncc(Br)c3n2)CC1] | 8-Bromo-N-(1-cyanocyclopropyl)pyrido[4,3-b]pyrazine-2-carboxamide | 2.32 |

TABLE 1-continued

List of examples and EC$_{150}$ data

| Example | Structure | Name | EC$_{150}$ (uM) |
|---|---|---|---|
| 4 | 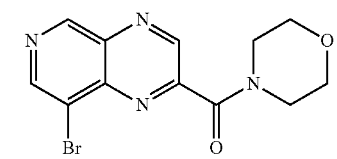 [SMILES: O=C(c1cnc2cncc(Br)c2n1)N1CCOCC1] | (8-Bromopyrido[4,3-b]pyrazin-2-yl)(morpholino)methanone | 0.07 |
| 5 | 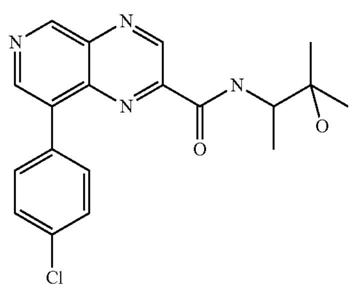 [SMILES: CC(NC(=O)c1cnc2cncc(-c3ccc(Cl)cc3)c2n1)C(C)(C)O] | 8-(4-Chlorophenyl)-N-(3-hydroxy-3-methylbutan-2-yl)pyrido[4,3-b]pyrazine-2-carboxamide | 0.89 |
| 6 | 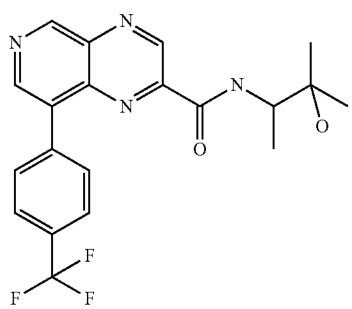 [SMILES: CC(NC(=O)c1cnc2cncc(-c3ccc(C(F)(F)F)cc3)c2n1)C(C)(C)O] | N-(3-Hydroxy-3-methylbutan-2-yl)-8-(4-(trifluoromethyl)phenyl)pyrido[4,3-b]pyrazine-2-carboxamide | 0.38 |
| 7 | 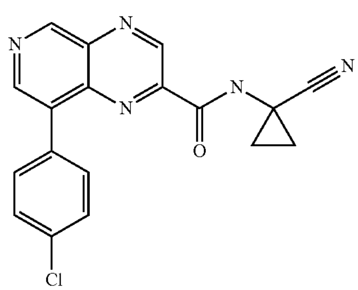 [SMILES: N#CC1(NC(=O)c2cnc3cncc(-c4ccc(Cl)cc4)c3n2)CC1] | 8-(4-Chlorophenyl)-N-(1-cyanocyclopropyl)pyrido[4,3-b]pyrazine-2-carboxamide | 0.39 |
| 8 | 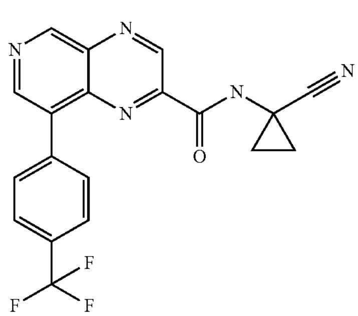 [SMILES: N#CC1(NC(=O)c2cnc3cncc(-c4ccc(C(F)(F)F)cc4)c3n2)CC1] | N-(1-Cyanocyclopropyl)-8-(4-(trifluoromethyl)phenyl)pyrido[4,3-b]pyrazine-2-carboxamide | 0.39 |

TABLE 1-continued

List of examples and EC$_{150}$ data

| Example | Structure | Name | EC$_{150}$ (uM) |
|---|---|---|---|
| 9 | 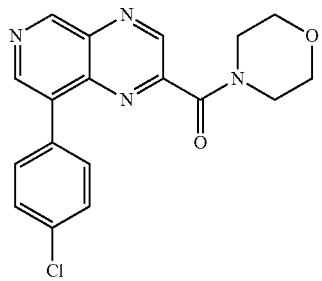 [SMILES: O=C(c1cnc2cncc(-c3ccc(Cl)cc3)c2n1)N1CCOCC1] | (8-(4-Chlorophenyl)pyrido[4,3-b]pyrazin-2-yl)(morpholino)methanone | 0.65 |
| 10 | 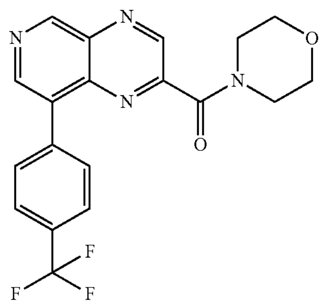 [SMILES: O=C(c1cnc2cncc(-c3ccc(C(F)(F)F)cc3)c2n1)N1CCOCC1] | Morpholino(8-(4-(trifluoromethyl)phenyl)pyrido[4,3-b]pyrazin-2-yl)methanone | 2.96 |
| 11 | 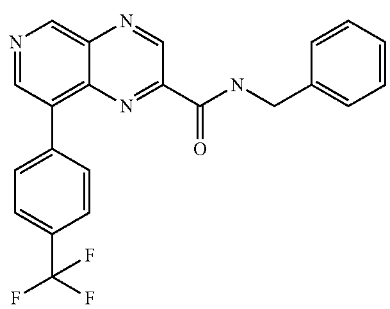 [SMILES: O=C(NCc1ccccc1)c1cnc2cncc(-c3ccc(C(F)(F)F)cc3)c2n1] | N-Benzyl-8-(4-(trifluoromethyl)phenyl)pyrido[4,3-b]pyrazine-2-carboxamide | 0.41 |
| 12 | 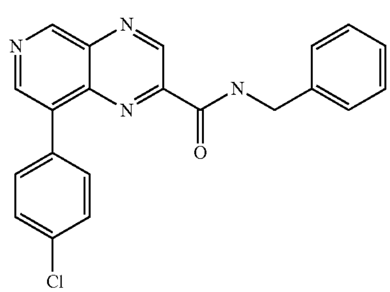 [SMILES: O=C(NCc1ccccc1)c1cnc2cncc(-c3ccc(Cl)cc3)c2n1] | N-Benzyl-8-(4-chlorophenyl)pyrido[4,3-b]pyrazine-2-carboxamide | 0.26 |
| 13 | 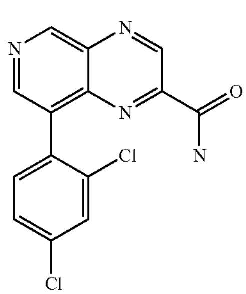 [SMILES: NC(=O)c1cnc2cncc(-c3ccc(Cl)cc3Cl)c2n1] | 8-(2,4-Dichlorophenyl)pyrido[4,3-b]pyrazine-2-carboxamide | 0.28 |

TABLE 1-continued

List of examples and EC$_{150}$ data

| Example | Structure | Name | EC$_{150}$ (uM) |
|---|---|---|---|
| 14 | 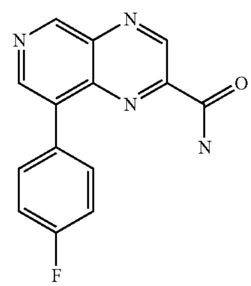 [SMILES: NC(=O)c1cnc2cncc(-c3ccc(F)cc3)c2n1] | 8-(4-Fluorophenyl)pyrido[4,3-b]pyrazine-2-carboxamide | 0.10 |
| 15 | 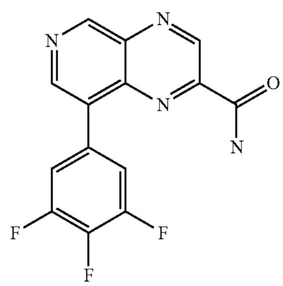 [SMILES: NC(=O)c1cnc2cncc(-c3cc(F)c(F)c(F)c3)c2n1] | 8-(3,4,5-Trifluorophenyl)pyrido[4,3-b]pyrazine-2-carboxamide | 0.55 |
| 16 | 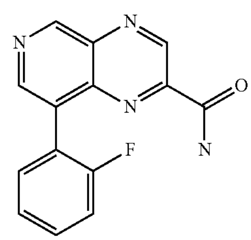 [SMILES: NC(=O)c1cnc2cncc(-c3ccccc3F)c2n1] | 8-(2-Fluorophenyl)pyrido[4,3-b]pyrazine-2-carboxamide | 0.06 |
| 17 | 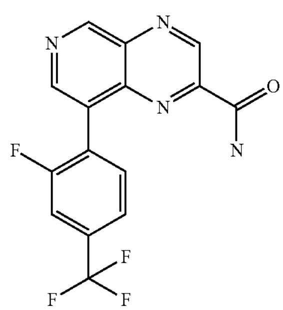 [SMILES: NC(=O)c1cnc2cncc(-c3ccc(C(F)(F)F)cc3F)c2n1] | 8-(2-Fluoro-4-(trifluoromethyl)phenyl)pyrido[4,3-b]pyrazine-2-carboxamide | 0.08 |
| 18 | 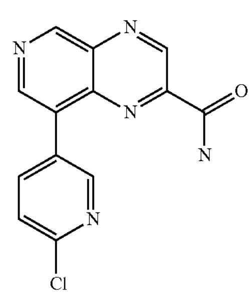 [SMILES: NC(=O)c1cnc2cncc(-c3ccc(Cl)nc3)c2n1] | 8-(6-Chloropyridin-3-yl)pyrido[4,3-b]pyrazine-2-carboxamide | 0.21 |

TABLE 1-continued

List of examples and EC$_{150}$ data

| Example | Structure | Name | EC$_{150}$ (uM) |
|---|---|---|---|
| 19 | 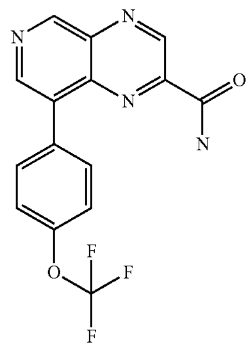 [SMILES: NC(=O)c1cnc2cncc(-c3ccc(OC(F)(F)F)cc3)c2n1] | 8-(4-(Trifluoromethoxy)phenyl)pyrido[4,3-b]pyrazine-2-carboxamide | 0.09 |
| 20 | 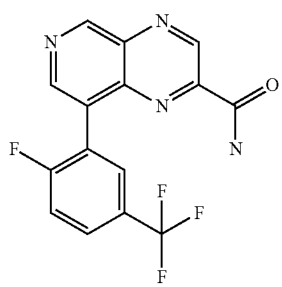 [SMILES: NC(=O)c1cnc2cncc(-c3cc(C(F)(F)F)ccc3F)c2n1] | 8-(2-Fluoro-5-(trifluoromethyl)phenyl)pyrido[4,3-b]pyrazine-2-carboxamide | 0.22 |
| 21 | 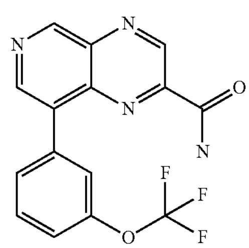 [SMILES: NC(=O)c1cnc2cncc(-c3cccc(OC(F)(F)F)c3)c2n1] | 8-(3-(Trifluoromethoxy)phenyl)pyrido[4,3-b]pyrazine-2-carboxamide | 0.21 |
| 22 | 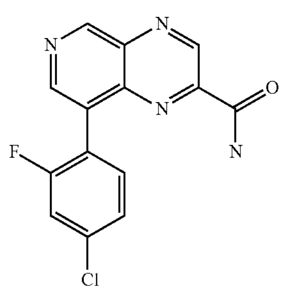 [SMILES: NC(=O)c1cnc2cncc(-c3ccc(Cl)cc3F)c2n1] | 8-(4-Chloro-2-fluorophenyl)pyrido[4,3-b]pyrazine-2-carboxamide | 0.07 |
| 23 | 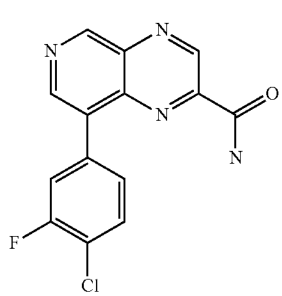 [SMILES: NC(=O)c1cnc2cncc(-c3ccc(Cl)c(F)c3)c2n1] | 8-(4-Chloro-3-fluorophenyl)pyrido[4,3-b]pyrazine-2-carboxamide | 0.10 |

TABLE 1-continued

List of examples and EC$_{150}$ data

| Example | Structure | Name | EC$_{150}$ (uM) |
|---|---|---|---|
| 24 | 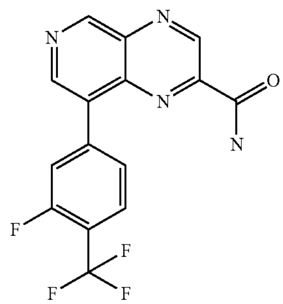 [SMILES: NC(=O)c1cnc2cncc(-c3ccc(C(F)(F)F)c(F)c3)c2n1] | 8-(3-Fluoro-4-(trifluoromethyl)phenyl)pyrido[4,3-b]pyrazine-2-carboxamide | 0.18 |
| 25 | 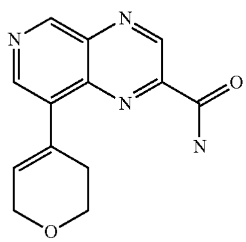 [SMILES: NC(=O)c1cnc2cncc(C3=CCOCC3)c2n1] | 8-(3,6-Dihydro-2H-pyran-4-yl)pyrido[4,3-b]pyrazine-2-carboxamide | 0.66 |
| 26 | 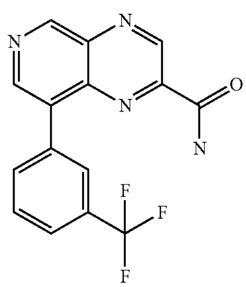 [SMILES: NC(=O)c1cnc2cncc(-c3cccc(C(F)(F)F)c3)c2n1] | 8-(3-(Trifluoromethyl)phenyl)pyrido[4,3-b]pyrazine-2-carboxamide | 0.43 |
| 27 | 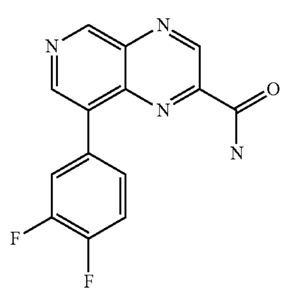 [SMILES: NC(=O)c1cnc2cncc(-c3ccc(F)c(F)c3)c2n1] | 8-(3,4-Difluorophenyl)pyrido[4,3-b]pyrazine-2-carboxamide | 0.12 |
| 28 | 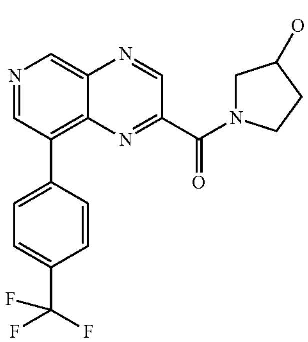 [SMILES: O=C(c1cnc2cncc(-c3ccc(C(F)(F)F)cc3)c2n1)N1CCC(O)C1] | (3-Hydroxypyrrolidin-1-yl)(8-(4-(trifluoromethyl)phenyl)pyrido[4,3-b]pyrazin-2-yl)methanone | 0.29 |

TABLE 1-continued

List of examples and EC₁₅₀ data

| Example | Structure | Name | EC₁₅₀ (uM) |
|---|---|---|---|
| 29 | 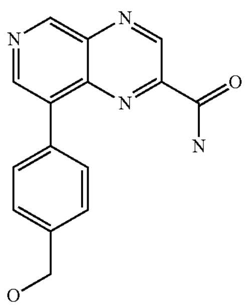 [SMILES: NC(=O)c1cnc2cncc(-c3ccc(CO)cc3)c2n1] | 8-(4-(Hydroxymethyl)phenyl)pyrido[4,3-b]pyrazine-2-carboxamide | 0.05 |
| 30 | 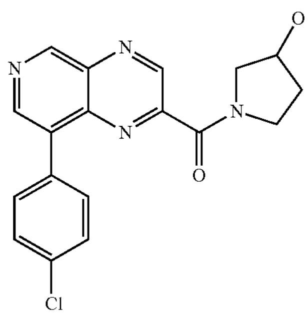 [SMILES: O=C(c1cnc2cncc(-c3ccc(Cl)cc3)c2n1)N1CCC(O)C1] | (8-(4-Chlorophenyl)pyrido[4,3-b]pyrazin-2-yl)(3-hydroxypyrrolidin-1-yl)methanone | 0.69 |
| 31 | 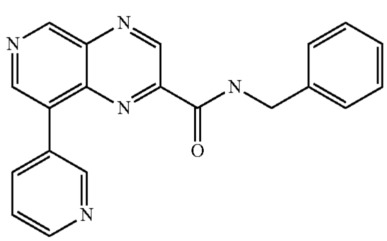 [SMILES: O=C(NCc1ccccc1)c1cnc2cncc(-c3cccnc3)c2n1] | N-Benzyl-8-(pyridin-3-yl)pyrido[4,3-b]pyrazine-2-carboxamide | 0.47 |
| 32 | 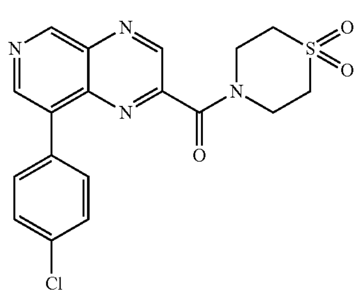 [SMILES: O=C(c1cnc2cncc(-c3ccc(Cl)cc3)c2n1)N1CCS(=O)(=O)CC1] | [8-(4-Chlorophenyl)pyrido[3,4-b]pyrazin-2-yl]-(1,1-dioxo-1,4-thiazinan-4-yl)methanone | 0.84 |
| 33 | 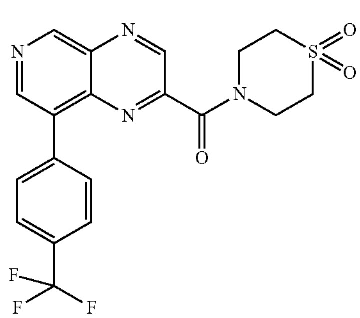 [SMILES: O=C(c1cnc2cncc(-c3ccc(C(F)(F)F)cc3)c2n1)N1CCS(=O)(=O)CC1] | (1,1-Dioxo-1,4-thiazinan-4-yl)-[8-[4-(trifluoromethyl)phenyl]pyrido[3,4-b]pyrazin-2-yl]methanone | 1.65 |

TABLE 1-continued

List of examples and EC$_{150}$ data

| Example | Structure | Name | EC$_{150}$ (uM) |
|---|---|---|---|
| 34 | 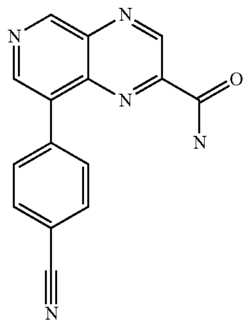 [SMILES: N#Cc1ccc(-c2cncc3ncc(C(N)=O)nc23)cc1] | 8-(4-Cyanophenyl)pyrido[4,3-b]pyrazine-2-carboxamide | 0.15 |
| 35 | 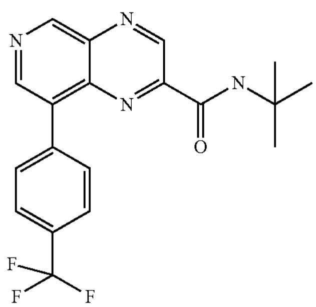 [SMILES: CC(C)(C)NC(=O)c1cnc2cncc(-c3ccc(C(F)(F)F)cc3)c2n1] | N-tert-Butyl-8-(4-(trifluoromethyl)phenyl)pyrido[4,3-b]pyrazine-2-carboxamide | 0.32 |
| 36 | 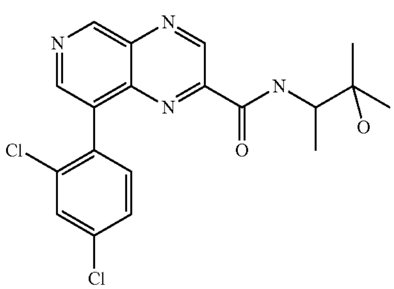 [SMILES: CC(NC(=O)c1cnc2cncc(-c3ccc(Cl)cc3Cl)c2n1)C(C)(C)O] | 8-(2,4-Dichlorophenyl)-N-(3-hydroxy-3-methylbutan-2-yl)pyrido[4,3-b]pyrazine-2-carboxamide | 1.50 |
| 37 | 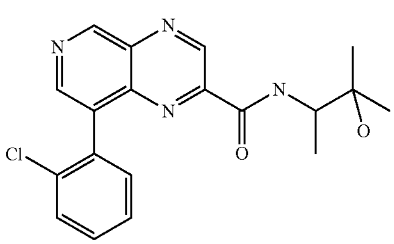 [SMILES: CC(NC(=O)c1cnc2cncc(-c3ccccc3Cl)c2n1)C(C)(C)O] | 8-(2-Chlorophenyl)-N-(3-hydroxy-3-methylbutan-2-yl)pyrido[4,3-b]pyrazine-2-carboxamide | 1.13 |
| 38 | 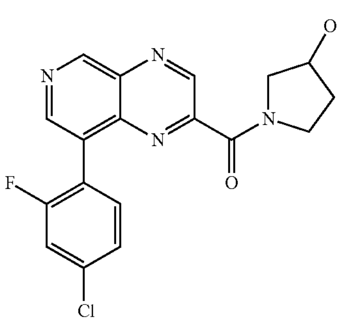 [SMILES: O=C(c1cnc2cncc(-c3ccc(Cl)cc3F)c2n1)N1CCC(O)C1] | (8-(4-Chloro-2-fluorophenyl)pyrido[4,3-b]pyrazin-2-yl)(3-hydroxypyrrolidin-1-yl)methanone | 0.10 |

TABLE 1-continued

List of examples and EC₁₅₀ data

| Example | Structure | Name | EC₁₅₀ (uM) |
|---|---|---|---|
| 39 | 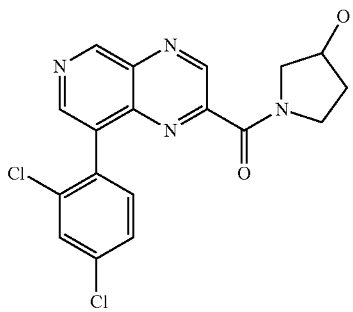 [SMILES: O=C(c1cnc2cncc(-c3ccc(Cl)cc3Cl)c2n1)N1CCC(O)C1] | (8-(2,4-Dichlorophenyl)pyrido[4,3-b]pyrazin-2-yl)(3-hydroxypyrrolidin-1-yl)methanone | 0.11 |
| 40 | 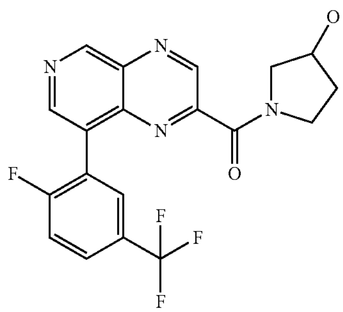 [SMILES: O=C(c1cnc2cncc(-c3cc(C(F)(F)F)ccc3F)c2n1)N1CCC(O)C1] | (8-(2-Fluoro-5-(trifluoromethyl)phenyl)pyrido[4,3-b]pyrazin-2-yl)(3-hydroxypyrrolidin-1-yl)methanone | 0.93 |
| 41 | 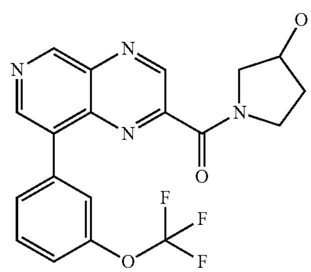 [SMILES: O=C(c1cnc2cncc(-c3cccc(OC(F)(F)F)c3)c2n1)N1CCC(O)C1] | (3-Hydroxypyrrolidin-1-yl)(8-(3-(trifluoromethoxy)phenyl)pyrido[4,3-b]pyrazin-2-yl)methanone | 0.60 |
| 42 | 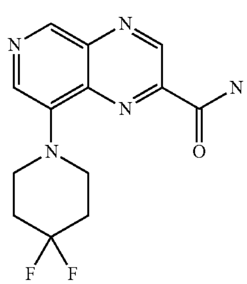 [SMILES: NC(=O)c1cnc2cncc(N3CCC(F)(F)CC3)c2n1] | 8-(4,4-Difluoropiperidin-1-yl)pyrido[4,3-b]pyrazine-2-carboxamide | 0.09 |
| 43 | 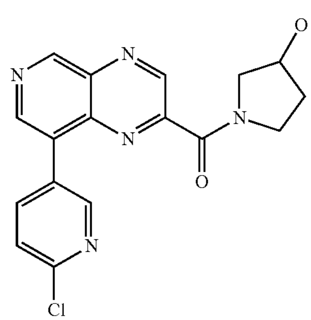 [SMILES: O=C(c1cnc2cncc(-c3ccc(Cl)nc3)c2n1)N1CCC(O)C1] | (8-(6-Chloropyridin-3-yl)pyrido[4,3-b]pyrazin-2-yl)(3-hydroxypyrrolidin-1-yl)methanone | 0.03 |

TABLE 1-continued

List of examples and EC150 data

| Example | Structure | Name | EC150 (uM) |
|---|---|---|---|
| 44 | 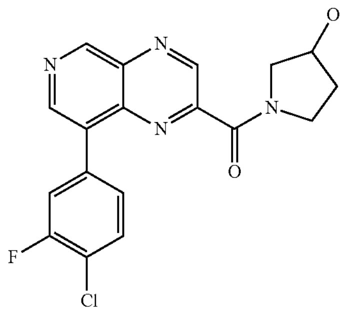 [SMILES: O=C(c1cnc2cncc(-c3ccc(Cl)c(F)c3)c2n1)N1CCC(O)C1] | (8-(4-Chloro-3-fluorophenyl)pyrido[4,3-b]pyrazin-2-yl)(3-hydroxypyrrolidin-1-yl)methanone | 0.27 |
| 45 | 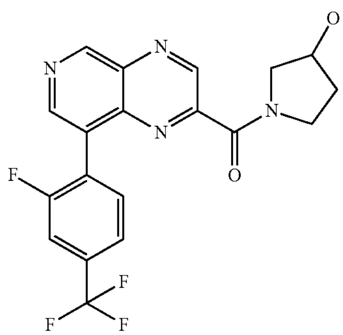 [SMILES: O=C(c1cnc2cncc(-c3ccc(C(F)(F)F)cc3F)c2n1)N1CCC(O)C1] | (8-(2-Fluoro-4-(trifluoromethyl)phenyl)pyrido[4,3-b]pyrazin-2-yl)(3-hydroxypyrrolidin-1-yl)methanone | 1.48 |
| 46 | 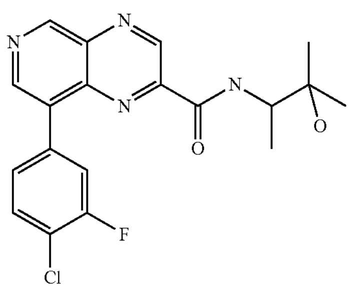 [SMILES: CC(NC(=O)c1cnc2cncc(-c3ccc(Cl)c(F)c3)c2n1)C(C)(C)O] | 8-(4-Chloro-3-fluorophenyl)-N-(3-hydroxy-3-methylbutan-2-yl)pyrido[4,3-b]pyrazine-2-carboxamide | 0.29 |
| 47 | 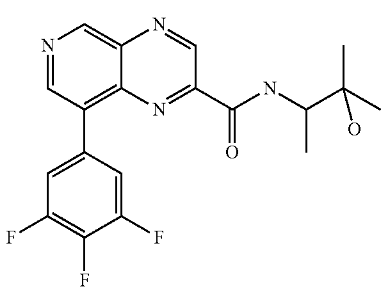 [SMILES: CC(NC(=O)c1cnc2cncc(-c3cc(F)c(F)c(F)c3)c2n1)C(C)(C)O] | N-(3-Hydroxy-3-methylbutan-2-yl)-8-(3,4,5-trifluorophenyl)pyrido[4,3-b]pyrazine-2-carboxamide | 0.03 |
| 48 | 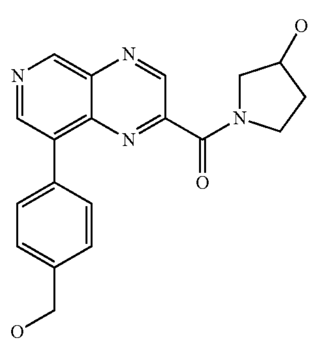 [SMILES: O=C(c1cnc2cncc(-c3ccc(CO)cc3)c2n1)N1CCC(O)C1] | (8-(4-(Hydroxymethyl)phenyl)pyrido[4,3-b]pyrazin-2-yl)(3-hydroxypyrrolidin-1-yl)methanone | 0.67 |

TABLE 1-continued

List of examples and EC$_{150}$ data

| Example | Structure | Name | EC$_{150}$ (uM) |
|---|---|---|---|
| 49 | 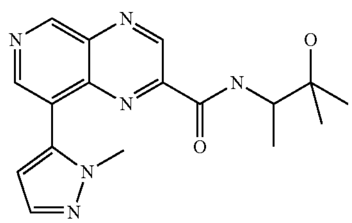 [SMILES: CC(NC(=O)c1cnc2cncc(-c3ccnn3C)c2n1)C(C)(C)O] | N-(3-Hydroxy-3-methylbutan-2-yl)-8-(1-methyl-1H-pyrazol-5-yl)pyrido[4,3-b]pyrazine-2-carboxamide | 0.02 |
| 50 | 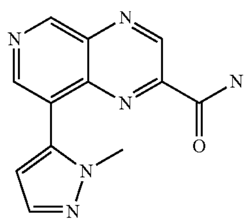 [SMILES: Cn1nccc1-c1cncc2ncc(C(N)=O)nc12] | 8-(1-Methyl-1H-pyrazol-5-yl)pyrido[4,3-b]pyrazine-2-carboxamide | 0.02 |
| 51 | 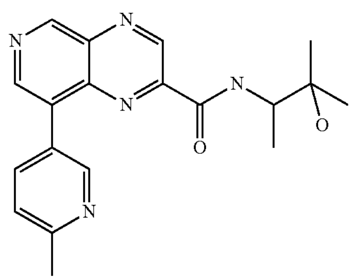 [SMILES: Cc1ccc(-c2cncc3ncc(C(=O)NC(C)C(C)(C)O)nc23)cn1] | N-(3-Hydroxy-3-methylbutan-2-yl)-8-(6-methylpyridin-3-yl)pyrido[4,3-b]pyrazine-2-carboxamide | 0.08 |
| 52 | 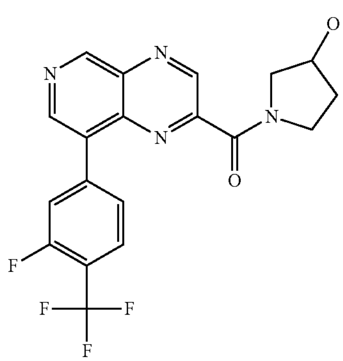 [SMILES: O=C(c1cnc2cncc(-c3ccc(C(F)(F)F)c(F)c3)c2n1)N1CCC(O)C1] | (8-(3-Fluoro-4-(trifluoromethyl)phenyl)pyrido[4,3-b]pyrazin-2-yl)(3-hydroxypyrrolidin-1-yl)methanone | 0.07 |
| 53 | 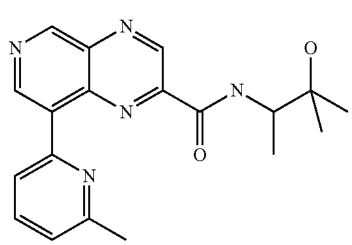 [SMILES: Cc1cccc(-c2cncc3ncc(C(=O)NC(C)C(C)(C)O)nc23)n1] | N-(3-Hydroxy-3-methylbutan-2-yl)-8-(6-methylpyridin-2-yl)pyrido[4,3-b]pyrazine-2-carboxamide | 0.50 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

Example 1

8-(4-Chlorophenyl)pyrido[4,3-b]pyrazine-2-carboxamide

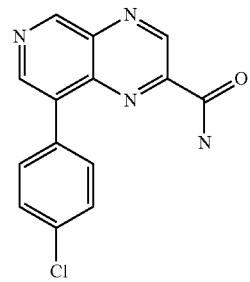

a) 8-Bromo-2-methylpyrido[4,3-b]pyrazine

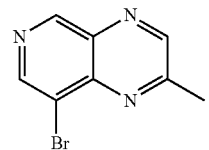

In a 50 ml round-bottomed flask, 5-bromopyridine-3,4-diamine (1.00 g, 5.32 mmol) and 2-oxopropanal (0.96 g, 5.32 mmol) were combined with dioxane (30.0 ml) to give a light brown solution. The reaction mixture was heated at 100° C. for 5 days. The crude reaction mixture was concentrated in vacuo and purified by chromatography (silica gel, ethyl acetate/heptane=50:50 to 100:0) to yield the title compound (1.00 g, 84%) as light brown solid. MS: m/e=224.3, 226.3 [M+H]$^+$.

b) 8-(4-Chlorophenyl)-2-methylpyrido[4,3-b]pyrazine

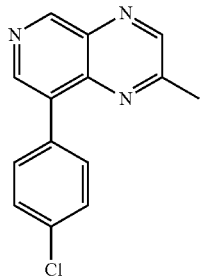 [SMILES: Cc1cnc2cncc(-c3ccc(Cl)cc3)c2n1]

In a 25 ml round-bottomed flask, 8-bromo-2-methylpyrido[4,3-b]pyrazine (500 mg, 2.23 mmol), 4-chlorophenylboronic acid (349 mg, 2.23 mmol) and cesium carbonate (800 mg, 2.45 mmol) were combined with dioxane (10 ml) and water (1.0 ml) to give a light brown solution. Bis(diphenylphosphino)ferrocene-palladium(II)dichloride (81.6 mg, 112 µmol) was added. The reaction mixture was heated at 80° C. for 2 hours. The crude reaction mixture was concentrated in vacuo and purified by chromatography (silica gel, ethyl acetate/heptane=20:80 to 100:0) to yield the title compound (618 mg, 92%) as light yellow solid. MS: m/e=256.4 [M+H]$^+$.

c) 8-(4-Chlorophenyl)pyrido[4,3-b]pyrazine-2-carboxylic acid

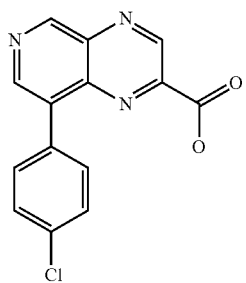 [SMILES: O=C(O)c1cnc2cncc(-c3ccc(Cl)cc3)c2n1]

In a 25 ml round-bottomed flask, 8-(4-chlorophenyl)-2-methylpyrido[4,3-b]pyrazine (610 mg, 2.39 mmol) and selenium dioxide (1.48 g, 13.4 mmol) were combined with dioxane (13 ml) to give a light yellow mixture. The reaction mixture was heated at 100° C. for 3 hours. The mixture was filtered through sintered glass and was concentrated in vacuo. The crude material was purified by chromatography (silica gel, methanol/dichloromethane=0:100 to 2:98). The pure fractions were concentrated in vacuo and were combined with t-butanol (13 ml) and 2-methylbut-2-ene (4 ml) to give a light yellow solution. Sodium chlorite (1.6 g, 17.7 mmol) and sodium dihydrogen phosphate (1.6 g, 13.4 mmol) in water (13 ml) were added slowly and the mixture was stirred at room temperature overnight. The crude reaction mixture was concentrated in vacuo, triturated with water (13 ml) and stirred for 30 minutes at room temperature. The residue was filtered off and dried in vacuo to yield the title compound (295 mg, 43%) as light light yellow solid. MS: m/e=284.4 [M−H]$^-$.

d) 8-(4-Chlorophenyl)pyrido[4,3-b]pyrazine-2-carboxamide

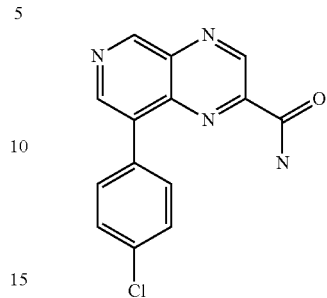

In a 25 ml round-bottomed flask, 8-(4-chlorophenyl)pyrido[4,3-b]pyrazine-2-carboxylic acid (195 mg, 683 µmol) and 1,1'-carbonyldiimidazole (133 mg, 819 µmol) were combined with dichloromethane (10 ml) to give a light yellow suspension. After 1 hour ammonium chloride (183 mg, 3.41 mmol) and triethylamine (345 mg, 476 µl, 3.41 mmol) were added. The mixture was stirred at room temperature overnight. Then ammonium chloride (183 mg, 3.41 mmol) and triethylamine (345 mg, 476 µl, 3.41 mmol) were added again and the mixture was stirred at room temperature for 3 days. Chromatography (silica gel, ethyl acetate/heptane=10:90 to 100:0) and trituration with diethyl ether/pentane (0.5 ml/0.5 ml yielded the title compound (126 mg, 65%) as light yellow solid. MS: m/e=285.3 [M+H]$^+$.

Example 2

8-(4-(Trifluoromethyl)phenyl)pyrido[4,3-b]pyrazine-2-carboxamide

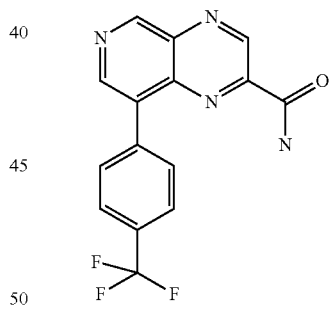

a) 8-Bromopyrido[4,3-b]pyrazine-2-carboxylic acid

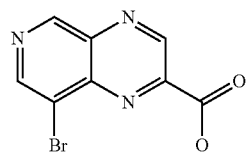 [SMILES: O=C(O)c1cnc2cncc(Br)c2n1]

In a 25 ml round-bottomed flask, 8-bromo-2-methylpyrido[4,3-b]pyrazine (500 mg, 2.23 mmol) and selenium dioxide (1.39 g, 12.5 mmol) were combined with dioxane (10 ml) to give a light yellow mixture. The reaction mixture was heated at 100° C. for 3 hours. The mixture was filtered and was concentrated in vacuo. The crude material was purified by chromatography (silica gel, methanol/dichloromethane=0:100 to 2:98). The pure fractions were concentrated in vacuo and were combined with t-butanol (10 ml) and 2-methylbut-2-ene (3 ml) to give a light yellow solution. Sodium chlorite (1.5 g, 16.6 mmol) and sodium dihydrogen phosphate (1.5 g, 12.5 mmol) in water (10 ml) were added slowly and the mixture was stirred at room temperature over weekend. The crude reaction mixture was concentrated in vacuo, triturated with water at room temperature for 15 minutes. The residue was filtered off and dried in vacuo to yield the title compound (329 mg, 58%) as light brown solid. MS: m/e=252.3, 254.3 [M−H]⁻.

b) 8-Bromopyrido[4,3-b]pyrazine-2-carboxamide

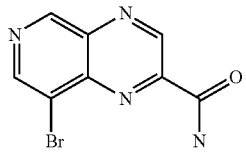 [SMILES: NC(=O)c1cnc2cncc(Br)c2n1]

In a 50 ml round-bottomed flask, 8-bromopyrido[4,3-b]pyrazine-2-carboxylic acid (324 mg, 1.28 mmol) and 1,1'-carbonyldiimidazole (227 mg, 1.4 mmol) were combined with dichloromethane (10 ml) to give a brown suspension. The mixture was stirred for 1 hour at room temperature. Then ammonium chloride (341 mg, 6.38 mmol) and triethylamine (645 mg, 889 µl, 6.38 mmol) were added and stirring was continued for 3 hours. The crude reaction mixture was concentrated in vacuo and purified by chromatography (silica gel, ethyl acetate/heptane=50:50 to 100:0) to yield the title compound (65 mg, 20%) as light brown solid. MS: m/e=253.3, 255.3 [M+H]⁺.

c) 8-(4-(Trifluoromethyl)phenyl)pyrido[4,3-b]pyrazine-2-carboxamide

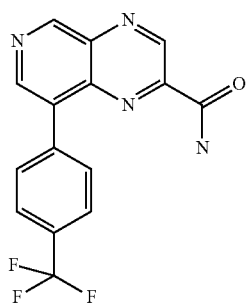 [SMILES: NC(=O)c1cnc2cncc(-c3ccc(C(F)(F)F)cc3)c2n1]

In a 25 ml round-bottomed flask, 8-bromopyrido[4,3-b]pyrazine-2-carboxamide (60 mg, 237 µmol), 4-(trifluoromethyl)phenylboronic acid (45.0 mg, 237 µmol) and cesium carbonate (77.3 mg, 237 µmol) were combined with dioxane (10 ml) and water (1.0 ml) to give a light brown solution. Bis(diphenylphosphino)ferrocene-palladium(II)dichloride (173 mg, 237 µmol) was added. The reaction mixture was heated to 80° C. and stirred for 2 hours. The crude reaction mixture was concentrated in vacuo and purified by flash chromatography (silica gel, ethyl acetate/heptane=50:50 to 100:0). Trituration with diethyl ether (1 ml) yielded the title compound (33 mg, 44%) as off-white solid. MS: m/e=319.4 [M+H]⁺.

Example 3

8-Bromo-N-(1-cyanocyclopropyl)pyrido[4,3-b]pyrazine-2-carboxamide

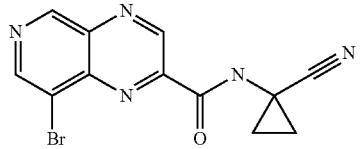 [SMILES: N#CC1(NC(=O)c2cnc3cncc(Br)c3n2)CC1]

In a 50 ml round-bottomed flask, 8-bromopyrido[4,3-b]pyrazine-2-carboxylic acid (300 mg, 1.18 mmol), 1-aminocyclopropanecarbonitrile (97.0 mg, 1.18 mmol) and triethylamine (179 mg, 247 µl) were combined with dimethylformamide (10.0 ml) to give a light brown solution. O-(7-Azabenzotriazol-1-yl)-N,N,N',N'-tetramethyluronium hexafluorophosphate (HATU, 494 mg, 1.3 mmol) was added and stirring was continued at room temperature. The reaction was complete after 1 hour. The crude reaction mixture was concentrated in vacuo. Extraction and chromatography (silica gel, ethyl acetate/heptane=50:50 to 100:0) yielded the title compound (220 mg, 59%) as off-white solid. MS: m/e=319.4 [M+H]⁺.

Example 4

(8-Bromopyrido[4,3-b]pyrazin-2-yl)(morpholino)methanone

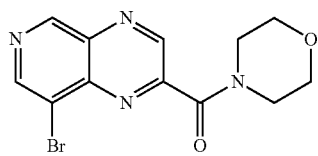 [SMILES: O=C(c1cnc2cncc(Br)c2n1)N1CCOCC1]

In a 50 ml round-bottomed flask, 8-bromopyrido[4,3-b]pyrazine-2-carboxylic acid (300 mg, 1.18 mmol), morpholine (103 mg, 103 µl 1.18 mmol) and triethylamine (179 mg, 247 µl, 1.77 mmol) were combined with dimethylformamide (10 ml) to give a light brown suspension. O-(7-Azabenzotriazol-1-yl)-N,N,N',N'-tetramethyluronium hexafluorophosphate (HATU, 494 mg, 1.3 mmol) was added and stirring was continued at room temperature. The reaction was complete after 1 hour. Extraction with ethyl acetate and chromatography (silica gel, ethyl acetate/heptane=50:50 to 100:0) yielded the title compound (240 mg, 63%) as off-white solid. MS: m/e=323.4, 235.4 [M+H]⁺.

Example 5

8-(4-Chlorophenyl)-N-(3-hydroxy-3-methylbutan-2-yl)pyrido[4,3-b]pyrazine-2-carboxamide

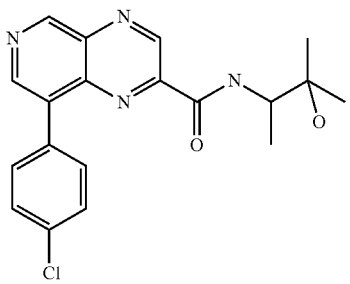

a) 8-Bromo-N-(3-hydroxy-3-methylbutan-2-yl)pyrido[4,3-b]pyrazine-2-carboxamide

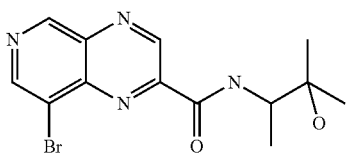 [SMILES: CC(NC(=O)c1cnc2cncc(Br)c2n1)C(C)(C)O]

In a 25 ml round-bottomed flask, 8-bromopyrido[4,3-b]pyrazine-2-carboxylic acid (300 mg, 1.18 mmol), 3-amino-2-methylbutan-2-ol (122 mg, 1.18 mmol) and triethylamine (179 mg, 247 µl, 1.77 mmol) were combined with dimethylformamide (10 ml) to give a light brown solution. Azabenzotriazol-1-yl)-N,N,N',N'-tetramethyluronium hexafluorophosphate (HATU, 494 mg, 1.3 mmol) was added and stirring was continued at room temperature overnight. Extraction with ethyl acetate and chromatography (silica gel, ethyl acetate/heptane=50:50 to 100:0) yielded the title compound (218 mg, 54%) as light brown solid. MS: m/e=339.0, 341.0 [M+H]+.

b) 8-(4-Chlorophenyl)-N-(3-hydroxy-3-methylbutan-2-yl)pyrido[4,3-b]pyrazine-2-carboxamide

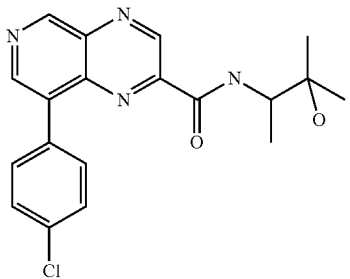 [SMILES: CC(NC(=O)c1cnc2cncc(-c3ccc(Cl)cc3)c2n1)C(C)(C)O]

In a 25 ml round-bottomed flask, 8-bromo-N-(3-hydroxy-3-methylbutan-2-yl)pyrido[4,3-b]pyrazine-2-carboxamide (50 mg, 147 µmol), 4-chlorophenylboronic acid (23.1 mg, 147 µmol) and cesium carbonate (96.1 mg, 295 µmol) were combined with dioxane (2.0 ml) and water (200 µl) to give a light brown solution. Bis(diphenylphosphino)ferrocene-palladium(II)dichloride (10.8 mg, 14.7 µmol) was added. The reaction mixture was heated at 80° C. for 1 hour. The crude material was purified by chromatography (silica gel, ethyl acetate/heptane=20:80 to 100:0) to yield the title compound (52.3 mg, 96%) as yellow solid. MS: m/e=371.5 [M+H]+.

Example 6

N-(3-Hydroxy-3-methylbutan-2-yl)-8-(4-(trifluoromethyl)phenyl)pyrido[4,3-b]pyrazine-2-carboxamide

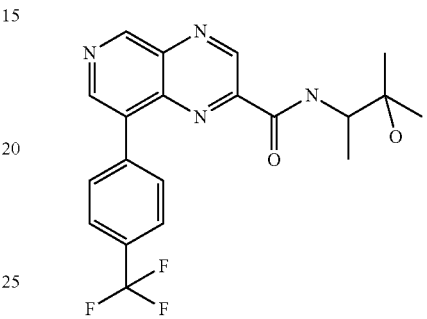

In a 25 ml round-bottomed flask, 8-bromo-N-(3-hydroxy-3-methylbutan-2-yl)pyrido[4,3-b]pyrazine-2-carboxamide (50 mg, 147 µmol), 4-(trifluoromethyl)phenylboronic acid (28.0 mg, 147 µmol) and cesium carbonate (96.1 mg, 295 µmol) were combined with dioxane (2.0 ml) and water (200 µl) to give a light brown solution. Bis(diphenylphosphino)ferrocene-palladium(II)dichloride (10.8 mg, 14.7 µmol) was added. The reaction mixture was heated at 80° C. for 1 hour. The crude material was purified by chromatography (silica gel, ethyl acetate/heptane=20:80 to 100:0) to yield the title compound (58.2 mg, 98%) as yellow solid. MS: m/e=405.6 [M+H]+.

Example 7

8-(4-Chlorophenyl)-N-(1-cyanocyclopropyl)pyrido[4,3-b]pyrazine-2-carboxamide

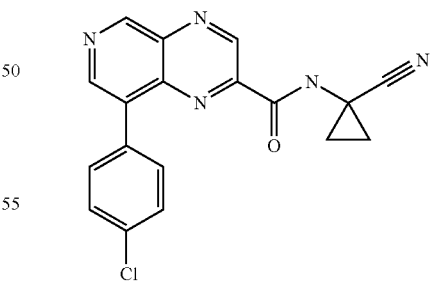

In a 25 ml round-bottomed flask, 8-bromo-N-(1-cyanocyclopropyl)pyrido[4,3-b]pyrazine-2-carboxamide (50 mg, 157 µmol), 4-chlorophenylboronic acid (24.6 mg, 157 µmol) and cesium carbonate (102 mg, 314 µmol) were combined with dioxane (2.0 ml) and water (200 µl) to give a colorless solution. Bis(diphenylphosphino)ferrocene-palladium(II)dichloride (11.5 mg, 15.7 µmol) was added. The reaction mixture was heated at 80° C. for 30 minutes. The crude Example 8

N-(1-Cyanocyclopropyl)-8-(4-(trifluoromethyl)phenyl)pyrido[4,3-b]pyrazine-2-carboxamide

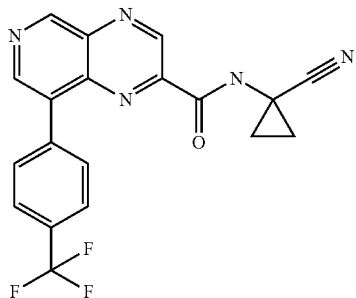 [SMILES: N#CC1(NC(=O)c2cnc3cncc(-c4ccc(C(F)(F)F)cc4)c3n2)CC1]

In a 25 ml round-bottomed flask, 8-bromo-N-(1-cyanocyclopropyl)pyrido[4,3-b]pyrazine-2-carboxamide (50 mg, 157 µmol), 4-(trifluoromethyl)phenylboronic acid (29.9 mg, 157 µmol) and cesium carbonate (102 mg, 314 µmol, Eq: 2.00) were combined with dioxane (2.0 ml) and water (200 µl) to give a colorless solution. Bis(diphenylphosphino)ferrocene-palladium(II)dichloride (11.5 mg, 15.7 µmol) was added. The reaction mixture was heated at 80° C. for 30 minutes. The crude material was purified by chromatography (silica gel, ethyl acetate/heptane=20:80 to 100:0) to yield the title compound (54.7 mg, 76%) as off-white solid. MS: m/e=384.5 [M+H]$^+$.

Example 9

(8-(4-Chlorophenyl)pyrido[4,3-b]pyrazin-2-yl)(morpholino)methanone

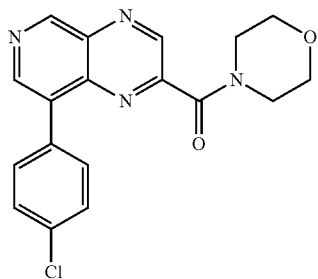 [SMILES: O=C(c1cnc2cncc(-c3ccc(Cl)cc3)c2n1)N1CCOCC1]

In a 25 ml round-bottomed flask, (8-bromopyrido[4,3-b]pyrazin-2-yl)(morpholino) methanone (50 mg, 155 µmol), 4-chlorophenylboronic acid (24.2 mg, 155 µmol) and cesium carbonate (101 mg, 309 µmol) were combined with dioxane (2.0 ml) and water (200 µl) to give a light brown solution. Bis(diphenylphosphino)ferrocene-palladium(II)dichloride (11.3 mg, 15.5 µmol) was added. The reaction mixture was heated at 80° C. for 1 hour. The crude material was purified by chromatography (silica gel, ethyl acetate/heptane=20:80 to 100:0) to yield the title compound (44.7 mg, 81%) as off-white solid. MS: m/e=355.5 [M+H]$^+$.

Example 10

Morpholino(8-(4-(trifluoromethyl)phenyl)pyrido[4,3-b]pyrazin-2-yl)methanone

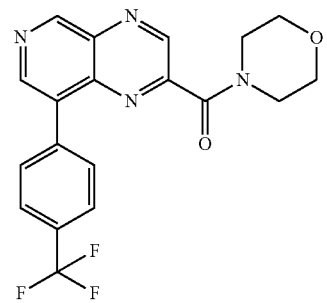

In a 25 ml round-bottomed flask, (8-bromopyrido[4,3-b]pyrazin-2-yl)(morpholino) methanone (50 mg, 155 µmol), 4-(trifluoromethyl)phenylboronic acid (29.4 mg, 155 µmol) and cesium carbonate (101 mg, 309 µmol) were combined with dioxane (2.0 ml) and water (200 µl) to give a light brown solution. Bis(diphenylphosphino)ferrocene-palladium(II)dichloride (11.3 mg, 15.5 µmol) was added. The reaction mixture was heated at 80° C. for 1 hour. The crude material was purified by chromatography (silica gel, ethyl acetate/heptane=20:80 to 100:0) to yield the title compound (51.7 mg, 86%) as off-white solid. MS: m/e=389.5 [M+H]$^+$.

Example 11

N-Benzyl-8-(4-(trifluoromethyl)phenyl)pyrido[4,3-b]pyrazine-2-carboxamide

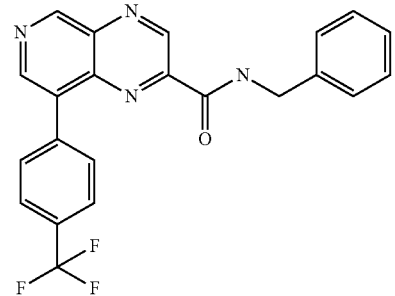 [SMILES: O=C(NCc1ccccc1)c1cnc2cncc(-c3ccc(C(F)(F)F)cc3)c2n1]

a) N-Benzyl-8-bromopyrido[4,3-b]pyrazine-2-carboxamide

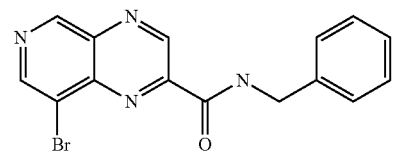 [SMILES: O=C(NCc1ccccc1)c1cnc2cncc(Br)c2n1]

In a 25 ml round-bottomed flask, 8-bromopyrido[4,3-b]pyrazine-2-carboxylic acid (170 mg, 669 µmol) and 3 drops of dimethylformamide were combined with dichloromethane (10 ml) to give a light brown suspension. Oxalyl chloride (849 mg, 586 μl, 6.69 mmol) was added and stirring was continued for 1 hour. The crude reaction mixture was concentrated in vacuo, taken up in dichloromethane (10 ml) and was added to a mix of phenylmethanamine (71.7 mg, 669 μmol) and triethylamine (135 mg, 187 μl, 1.34 mmol) in dichloromethane (10 ml). The reaction mixture was then stirred at room temperature over night. Extraction with dichloromethane and chromatography (silica gel, ethyl acetate/heptane=20:80 to 100:0) yielded the title compound (159 mg, 69%) as light brown solid. MS: m/e=343.5, 345.4 [M+H]⁺.

b) N-Benzyl-8-(4-(trifluoromethyl)phenyl)pyrido[4,3-b]pyrazine-2-carboxamide

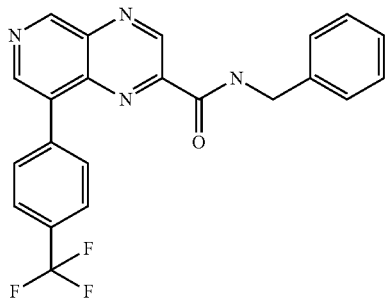

In a 25 ml round-bottomed flask, N-benzyl-8-bromopyrido[4,3-b]pyrazine-2-carboxamide (50 mg, 146 μmol), 4-(trifluoromethyl)phenylboronic acid (27.7 mg, 146 μmol) and cesium carbonate (94.9 mg, 291 μmol) were combined with dioxane (2.0 ml) and water (200 μl) to give a light yellow solution. Bis(diphenylphosphino)ferrocene-palladium(II)dichloride (10.7 mg, 14.6 μmol) was added. The reaction mixture was heated at 80° C. for 15 minutes. The crude material was purified by chromatography (silica gel, ethyl acetate/heptane=20:80 to 100:0) to yield the title compound (56.3 mg, 95%) as off-white solid. MS: m/e=409.6 [M+H]⁺.

Example 12

N-Benzyl-8-(4-chlorophenyl)pyrido[4,3-b]pyrazine-2-carboxamide

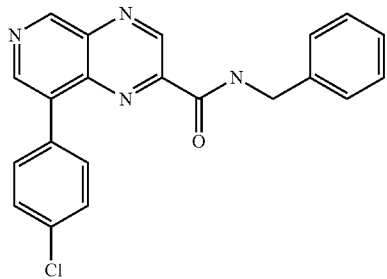

In a 25 ml round-bottomed flask, N-benzyl-8-bromopyrido[4,3-b]pyrazine-2-carboxamide (50 mg, 146 μmol), 4-chlorophenylboronic acid (22.8 mg, 146 μmol) and cesium carbonate (94.9 mg, 291 μmol) were combined with dioxane (2.0 ml) and water (200 μl) to give a light brown solution. Bis(diphenylphosphino)ferrocene-palladium(II)dichloride (10.7 mg, 14.6 μmol) was added. The reaction mixture was heated at 80° C. for 30 minutes. The crude material was purified by chromatography (silica gel, ethyl acetate/heptane=20:80 to 100:0) to yield the title compound (37.8 mg, 69%) as off-white solid. MS: m/e=375.5 [M+H]⁺.

Example 13

8-(2,4-Dichlorophenyl)pyrido[4,3-b]pyrazine-2-carboxamide

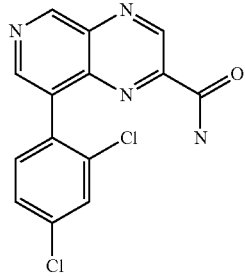 [SMILES: NC(=O)c1cnc2cncc(-c3ccc(Cl)cc3Cl)c2n1]

In a 25 ml round-bottomed flask, 8-bromopyrido[4,3-b]pyrazine-2-carboxamide (50 mg, 198 μmol), 2,4-dichlorophenylboronic acid (37.7 mg, 198 μmol) and cesium carbonate (129 mg, 395 μmol) were combined with dioxane (2.0 ml) and water (200 μl) to give a light brown solution. Bis(diphenylphosphino)ferrocene-palladium(II)dichloride (14.5 mg, 19.8 μmol) was added. The reaction mixture was heated at 80° C. and stirred for 30 minutes. The crude material was purified by chromatography (silica gel, ethyl acetate/heptane=20:80 to 100:0) to yield the title compound (51.2 mg, 81%) as off-white solid. MS: m/e=319.4, 321.4 [M+H]⁺.

Example 14

8-(4-Fluorophenyl)pyrido[4,3-b]pyrazine-2-carboxamide

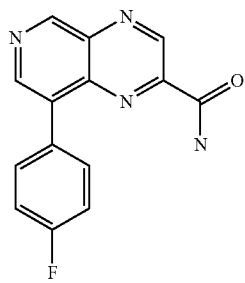 [SMILES: NC(=O)c1cnc2cncc(-c3ccc(F)cc3)c2n1]

In a 25 ml round-bottomed flask, 8-bromopyrido[4,3-b]pyrazine-2-carboxamide (50 mg, 198 μmol), 4-fluorophenylboronic acid (27.6 mg, 198 μmol) and cesium carbonate (129 mg, 395 μmol) were combined with dioxane (2.0 ml) and water (200 μl) to give a light brown solution. Bis(diphenylphosphino)ferrocene-palladium(II)dichloride (14.5 mg, 19.8 μmol) was added. The reaction mixture was heated at 80° C. for 30 minutes. The crude material was purified by chromatography (silica gel, ethyl acetate/heptane=20:80 to 100:0) to yield the title compound (33.4 mg, 63%) as yellow solid. MS: m/e=269.1 [M+H]⁺.

Example 15

8-(3,4,5-Trifluorophenyl)pyrido[4,3-b]pyrazine-2-carboxamide

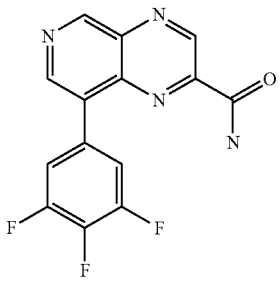 [SMILES: NC(=O)c1cnc2cncc(-c3cc(F)c(F)c(F)c3)c2n1]

In a 25 ml round-bottomed flask, 8-bromopyrido[4,3-b]pyrazine-2-carboxamide (50 mg, 198 µmol), 3,4,5-trifluorophenylboronic acid (34.8 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 30 minutes. The crude material was purified by chromatography (silica gel, ethyl acetate/heptane=20:80 to 100:0) to yield the title compound (49.6 mg, 83%) as light brown solid. MS: m/e=305.1 [M+H]⁺.

Example 16

8-(2-Fluorophenyl)pyrido[4,3-b]pyrazine-2-carboxamide

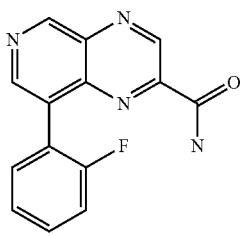 [SMILES: NC(=O)c1cnc2cncc(-c3ccccc3F)c2n1]

In a 25 ml round-bottomed flask, 8-bromopyrido[4,3-b]pyrazine-2-carboxamide (50 mg, 198 µmol), 2-fluorophenylboronic acid (27.6 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 1 hour. The crude material was purified by chromatography (silica gel, ethyl acetate/heptane=20:80 to 100:0) to yield the title compound (33 mg, 62%) as off-white solid. MS: m/e=269.1 [M+H]⁺.

Example 17

8-(2-Fluoro-4-(trifluoromethyl)phenyl)pyrido[4,3-b]pyrazine-2-carboxamide

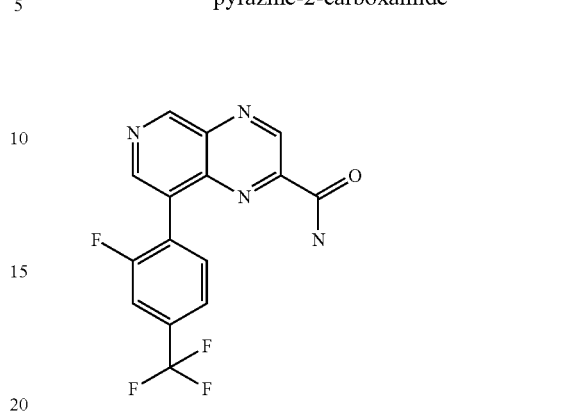

In a 25 ml round-bottomed flask, 8-bromopyrido[4,3-b]pyrazine-2-carboxamide (50 mg, 198 µmol), 2-fluoro-4-(trifluoromethyl)phenylboronic acid (41.1 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 30 minutes. The crude material was purified by chromatography (2×, silica gel, ethyl acetate/heptane=20:80 to 100:0) to yield the title compound (26 mg, 39%) as off-white solid. MS: m/e=337.1 [M+H]⁺.

Example 18

8-(6-Chloropyridin-3-yl)pyrido[4,3-b]pyrazine-2-carboxamide

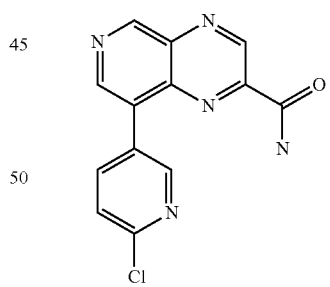

In a 25 ml round-bottomed flask, 8-bromopyrido[4,3-b]pyrazine-2-carboxamide (50 mg, 198 µmol), 6-chloropyridin-3-ylboronic acid (31.1 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 1 hour. The crude material was purified by chromatography (silica gel, ethyl acetate/heptane=20:80 to 100:0) to yield the title compound (48 mg, 85%) as light yellow solid. MS: m/e=286.1 [M+H]⁺.

Example 19

8-(4-(Trifluoromethoxy)phenyl)pyrido[4,3-b]pyrazine-2-carboxamide

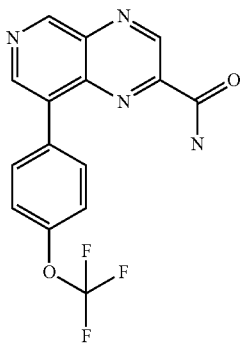 [SMILES: NC(=O)c1cnc2cncc(-c3ccc(OC(F)(F)F)cc3)c2n1]

In a 25 ml round-bottomed flask, 8-bromopyrido[4,3-b]pyrazine-2-carboxamide (50 mg, 198 µmol), 4-(trifluoromethoxy)phenylboronic acid (40.7 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 30 minutes. The crude material was purified by chromatography (2×, silica gel, ethyl acetate/heptane=20:80 to 100:0) to yield the title compound (21 mg, 32%) as off-white solid. MS: m/e=286.1 [M+H]$^+$.

Example 20

8-(2-Fluoro-5-(trifluoromethyl)phenyl)pyrido[4,3-b]pyrazine-2-carboxamide

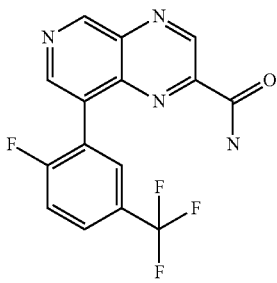

In a 25 ml round-bottomed flask, 8-bromopyrido[4,3-b]pyrazine-2-carboxamide (50 mg, 198 µmol), 2-fluoro-5-(trifluoromethyl)phenylboronic acid (41.1 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 30 minutes. The crude material was purified by chromatography (silica gel, ethyl acetate/heptane=20:80 to 100:0) to yield the title compound (40 mg, 60%) as off-white solid. MS: m/e=337.1 [M+H]$^+$.

Example 21

8-(3-(Trifluoromethoxy)phenyl)pyrido[4,3-b]pyrazine-2-carboxamide

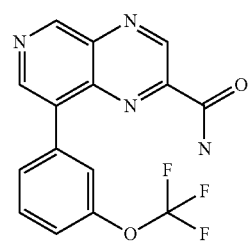 [SMILES: NC(=O)c1cnc2cncc(-c3cccc(OC(F)(F)F)c3)c2n1]

In a 25 ml round-bottomed flask, 8-bromopyrido[4,3-b]pyrazine-2-carboxamide (50 mg, 198 µmol), 3-(trifluoromethoxy)phenylboronic acid (40.7 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 30 minutes. The crude material was purified by chromatography (silica gel, ethyl acetate/heptane=20:80 to 100:0) to yield the title compound (40 mg, 61%) as off-white solid. MS: m/e=335.1 [M+H]$^+$.

Example 22

8-(4-Chloro-2-fluorophenyl)pyrido[4,3-b]pyrazine-2-carboxamide

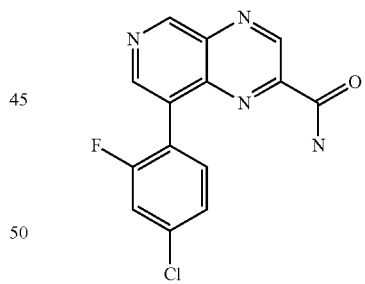

In a 25 ml round-bottomed flask, 8-bromopyrido[4,3-b]pyrazine-2-carboxamide (50 mg, 198 µmol), 4-chloro-2-fluorophenylboronic acid (34.5 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 30 minutes. The crude material was purified by chromatography (2×, silica gel, ethyl acetate/heptane=20:80 to 100:0) to yield the title compound (33 mg, 55%) as off-white solid. MS: m/e=303.1 [M+H]$^+$.

Example 23

8-(4-Chloro-3-fluorophenyl)pyrido[4,3-b]pyrazine-2-carboxamide

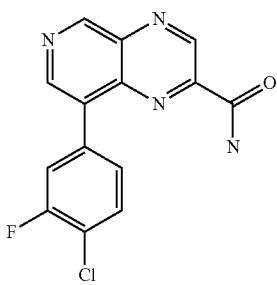 [SMILES: NC(=O)c1cnc2cncc(-c3ccc(Cl)c(F)c3)c2n1]

In a 25 ml round-bottomed flask, 8-bromopyrido[4,3-b]pyrazine-2-carboxamide (50 mg, 198 μmol), 4-chloro-3-fluorophenylboronic acid (34.5 mg, 198 μmol) and cesium carbonate (129 mg, 395 μmol) were combined with dioxane (2.0 ml) and water (200 μl) to give a light brown solution. Bis(diphenylphosphino)ferrocene-palladium(II)dichloride (14.5 mg, 19.8 μmol) was added. The reaction mixture was heated at 80° C. for 30 minutes. The crude material was purified by chromatography (silica gel, ethyl acetate/heptane=20:80 to 100:0) to yield the title compound (43.1 mg, 72%) as light brown solid. MS: m/e=303.1 [M+H]$^+$.

Example 24

8-(3-Fluoro-4-(trifluoromethyl)phenyl)pyrido[4,3-b]pyrazine-2-carboxamide

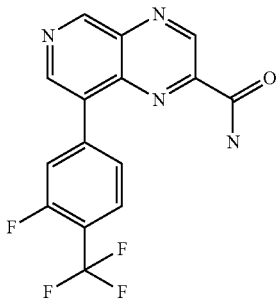

In a 25 ml round-bottomed flask, 8-bromopyrido[4,3-b]pyrazine-2-carboxamide (50 mg, 198 μmol), 3-fluoro-4-(trifluoromethyl)phenylboronic acid (41.1 mg, 198 μmol) and cesium carbonate (129 mg, 395 μmol) were combined with dioxane (2.0 ml) and water (200 μl) to give a light brown solution. Bis(diphenylphosphino)ferrocene-palladium(II)dichloride (14.5 mg, 19.8 μmol) was added. The reaction mixture was heated at 80° C. for 30 minutes. The crude material was purified by chromatography (silica gel, ethyl acetate/heptane=20:80 to 100:0) to yield the title compound (34.1 mg, 51%) as off-white solid. MS: m/e=337.1[M+H]$^+$.

Example 25

8-(3,6-Dihydro-2H-pyran-4-yl)pyrido[4,3-b]pyrazine-2-carboxamide

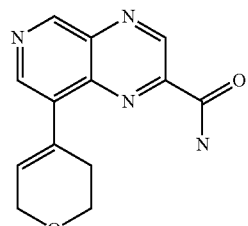

In a 25 ml round-bottomed flask, 8-bromopyrido[4,3-b]pyrazine-2-carboxamide (50 mg, 198 μmol), 3,6-dihydro-2H-pyran-4-ylboronic acid (25.3 mg, 198 μmol) and cesium carbonate (129 mg, 395 μmol) were combined with dioxane (2.0 ml) and water (200 μl) to give a light brown solution. Bis(diphenylphosphino)ferrocene-palladium(II)dichloride (14.5 mg, 19.8 μmol) was added. The reaction mixture was heated at 80° C. for 30 minutes. The crude material was purified by chromatography (silica gel, ethyl acetate/heptane=20:80 to 100:0) to yield the title compound (30 mg, 59%) as light yellow oil. MS: m/e=257.2[M+H]$^+$.

Example 26

8-(3-(Trifluoromethyl)phenyl)pyrido[4,3-b]pyrazine-2-carboxamide

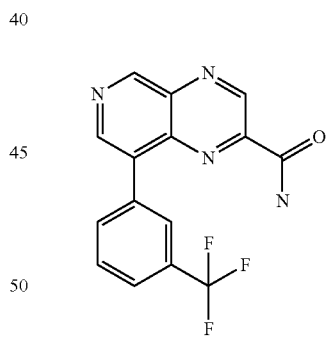

In a 25 ml round-bottomed flask, 8-bromopyrido[4,3-b]pyrazine-2-carboxamide (50 mg, 198 μmol), 3-(trifluoromethyl)phenylboronic acid (37.5 mg, 198 μmol) and cesium carbonate (129 mg, 395 μmol) were combined with dioxane (2.0 ml) and water (200 μl) to give a light brown solution. Bis(diphenylphosphino)ferrocene-palladium(II)dichloride (14.5 mg, 19.8 μmol) was added. The reaction mixture was heated at 80° C. for 30 min. The crude material was purified by chromatography (silica gel, ethyl acetate/heptane=20:80 to 100:0) to yield the title compound (25 mg, 40%) as off-white solid. MS: m/e=319.2[M+H]$^+$.

Example 27

8-(3,4-Difluorophenyl)pyrido[4,3-b]pyrazine-2-carboxamide

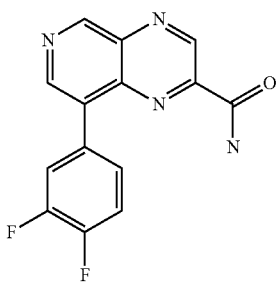 [SMILES: NC(=O)c1cnc2cncc(-c3ccc(F)c(F)c3)c2n1]

In a 25 ml round-bottomed flask, 8-bromopyrido[4,3-b]pyrazine-2-carboxamide (50 mg, 198 µmol), 3,4-difluorophenylboronic acid (31.2 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 30 minutes. The crude material was purified by chromatography (silica gel, ethyl acetate/heptane=20:80 to 100:0) to yield the title compound (37.8 mg, 67%) as light yellow solid. MS: m/e=287.1 [M+H]$^+$.

Example 28

(3-Hydroxypyrrolidin-1-yl)(8-(4-(trifluoromethyl)phenyl)pyrido[4,3-b]pyrazin-2-yl)methanone

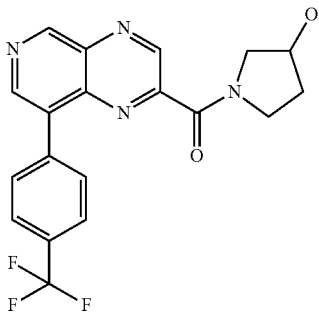 [SMILES: O=C(c1cnc2cncc(-c3ccc(C(F)(F)F)cc3)c2n1)N1CCC(O)C1]

a) (8-Bromopyrido[4,3-b]pyrazin-2-yl)(3-hydroxypyrrolidin-1-yl)methanone

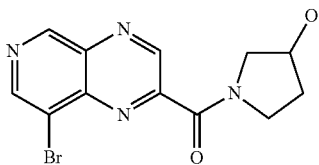 [SMILES: O=C(c1cnc2cncc(Br)c2n1)N1CCC(O)C1]

In a 50 ml round-bottomed flask, 8-bromopyrido[4,3-b]pyrazine-2-carboxylic acid (800 mg, 3.15 mmol), pyrrolidin-3-ol (274 mg, 3.15 mmol) and triethylamine (478 mg, 658 µl, 4.72 mmol) were combined with dimethylformamide (25.0 ml) to give a light brown solution. Azabenzotriazol-1-yl)-N,N,N',N'-tetramethyluronium hexafluorophosphate (HATU, 1.32 g, 3.46 mmol) was added and stirring was continued at room temperature over night. The crude reaction mixture was concentrated in vacuo and purified by chromatography (silica gel, ethyl acetate/heptane=50:50 to 100:0). Trituration with diethyl ether (2 ml) yielded the title compound (104 mg, 10%) as off-white solid. MS: m/e=323.0, 325.0 [M+H]$^+$.

b) (3-Hydroxypyrrolidin-1-yl)(8-(4-(trifluoromethyl)phenyl)pyrido[4,3-b]pyrazin-2-yl)methanone

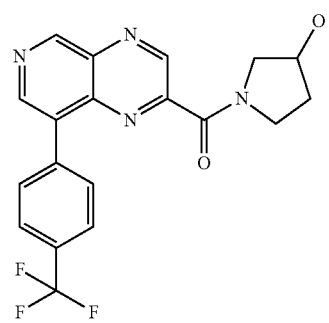 [SMILES: O=C(c1cnc2cncc(-c3ccc(C(F)(F)F)cc3)c2n1)N1CCC(O)C1]

In a 25 ml round-bottomed flask, (8-bromopyrido[4,3-b]pyrazin-2-yl)(3-hydroxypyrrolidin-1-yl)methanone (50 mg, 155 µmol), 4-(trifluoromethyl)phenylboronic acid (29.4 mg, 155 µmol) and cesium carbonate (55.5 mg, 170 µmol) were combined with dioxane (5.0 ml) and water (0.5 ml) to give a light brown solution. Bis(diphenylphosphino)ferrocene-palladium(II)dichloride (5.66 mg, 7.74 µmol) was added under Argon. The reaction mixture was heated at 90° C. for 1 hour. The crude material was concentrated in vacuo and purified by chromatography (silica gel, ethyl acetate/heptane=50:50 to 100:0) to yield the title compound (44.3 mg, 74%) as off-white solid. MS: m/e=389.2 [M+H]$^+$.

Example 29

8-(4-(Hydroxymethyl)phenyl)pyrido[4,3-b]pyrazine-2-carboxamide

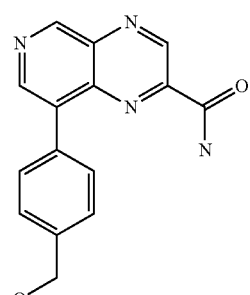

In a 25 ml round-bottomed flask, 8-bromopyrido[4,3-b]pyrazine-2-carboxamide (50 mg, 198 µmol), 4-(hydroxymethyl)phenylboronic acid (30.0 mg, 198 µmol) and cesium carbonate (129 mg, 395 µmol) were combined with dioxane (2.00 ml) and water (200 μl) to give a light brown solution. Bis(diphenylphosphino)ferrocene-palladium(II)dichloride (14.5 mg, 19.8 μmol) was added. The reaction mixture was heated at 80° C. for 30 minutes. The crude material was purified by chromatography (silica gel, ethyl acetate/heptane=20:80 to 100:0) to yield the title compound (18 mg, 33%) as light yellow solid. MS: m/e=281.2 [M+H]$^+$.

Example 30

(8-(4-Chlorophenyl)pyrido[4,3-b]pyrazin-2-yl)(3-hydroxypyrrolidin-1-yl)methanone

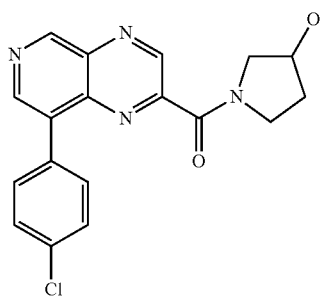 [SMILES: O=C(c1cnc2cncc(-c3ccc(Cl)cc3)c2n1)N1CCC(O)C1]

In a 25 ml round-bottomed flask, (8-bromopyrido[4,3-b]pyrazin-2-yl)(3-hydroxypyrrolidin-1-yl)methanone (54 mg, 167 μmol), 4-chlorophenylboronic acid (26.1 mg, 167 μmol) and cesium carbonate (59.9 mg, 184 μmol) were combined with dioxane (5.0 ml) and water (0.5 ml) to give a light brown solution. Bis(diphenylphosphino)ferrocene-palladium(II)dichloride (6.11 mg, 8.36 μmol) was added under Argon. The reaction mixture was heated at 90° C. for 1 hour. The crude material was concentrated in vacuo and purified by chromatography (silica gel, ethyl acetate/heptane=25:75 to 100:0) to yield the title compound (36.5 mg, 61%) as off-white solid. MS: m/e=355.2 [M+H]$^+$.

Example 31

N-Benzyl-8-(pyridin-3-yl)pyrido[4,3-b]pyrazine-2-carboxamide

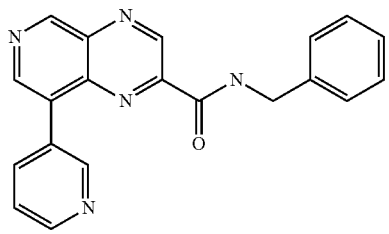 [SMILES: O=C(NCc1ccccc1)c1cnc2cncc(-c3cccnc3)c2n1]

In a 25 ml round-bottomed flask, N-benzyl-8-bromopyrido[4,3-b]pyrazine-2-carboxamide (45 mg, 131 μmol), pyridin-3-ylboronic acid (16.1 mg, 131 μmol) and cesium carbonate (47.0 mg, 144 μmol) were combined with dioxane (12.9 ml) and water (1.0 ml) to give a light brown suspension. Bis(diphenylphosphino)ferrocene-palladium(II) dichloride (4.8 mg, 6.56 μmol) was added. The reaction mixture was heated at 80° C. for 2 hours. The crude reaction mixture was concentrated in vacuo and purified by chromatography (silica gel, ethyl acetate/heptane=20:80 to 100:0) to yield the title compound (35 mg, 78%) as off-white solid. MS: m/e=342.2 [M+H]$^+$.

Example 32

[8-(4-Chlorophenyl)pyrido[3,4-b]pyrazin-2-yl]-(1,1-dioxo-1,4-thiazinan-4-yl)methanone

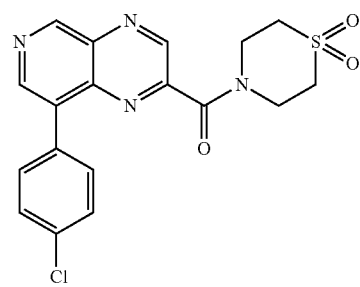 [SMILES: O=C(c1cnc2cncc(-c3ccc(Cl)cc3)c2n1)N1CCS(=O)(=O)CC1]

a) (8-Bromopyrido[3,4-b]pyrazin-2-yl)-(1,1-dioxo-1,4-thiazinan-4-yl)methanone

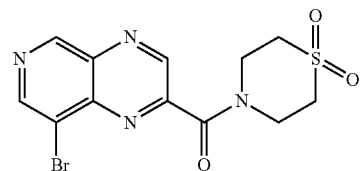 [SMILES: O=C(c1cnc2cncc(Br)c2n1)N1CCS(=O)(=O)CC1]

In a 50 ml round-bottomed flask, 8-bromopyrido[3,4-b]pyrazine-2-carboxylic acid (300 mg, 1.18 mmol), thiomorpholine-1,1-dioxide (160 mg, 1.18 mmol) and triethylamine (179 mg, 247 μl, 1.77 mmol) were combined with dimethylformamide (10.0 ml) to give a light brown suspension. Azabenzotriazol-1-yl)-N,N,N',N'-tetramethyluronium hexafluorophosphate (HATU, 494 mg, 1.3 mmol) was added and stirring was continued at room temperature for 4 hours. The crude reaction mixture was concentrated in vacuo and extracted with ethyl acetate/water. Purification by chromatography (silica gel, ethyl acetate/heptane=50:50 to 100:0) yielded the title compound (213 mg, 49%) as light brown solid. MS: m/e=373.1 [M+H]$^+$.

b) [8-(4-Chlorophenyl)pyrido[3,4-b]pyrazin-2-yl]-(1,1-dioxo-1,4-thiazinan-4-yl)methanone

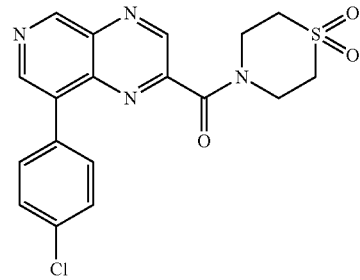

In a 25 ml round-bottomed flask, (8-bromopyrido[3,4-b]pyrazin-2-yl)-(1,1-dioxo-1,4-thiazinan-4-yl)methanone (70 mg, 189 µmol), 4-chlorophenylboronic acid (29.5 mg, 189 µmol) and cesium carbonate (67.6 mg, 207 µmol) were combined with dioxane (10 ml) and water (1.0 ml) to give a light brown suspension. Bis(diphenylphosphino)ferrocene-palladium(II)dichloride (6.9 mg, 9.43 µmol) was added. The reaction mixture was heated at 80° C. for 2 hours. The crude reaction mixture was concentrated in vacuo and purified by chromatography (silica gel, ethyl acetate/heptane=20:80 to 100:0) to yield the title compound (72 mg, 95%) as off-white solid. MS: m/e=403.1 [M+H]$^+$.

Example 33

(1,1-Dioxo-1,4-thiazinan-4-yl)-[8-[4-(trifluoromethyl)phenyl]pyrido[3,4-b]pyrazin-2-yl]methanone

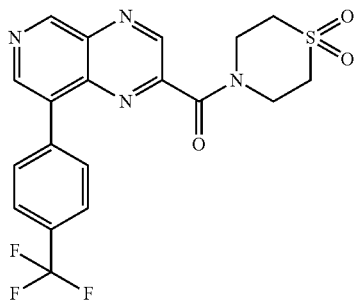 [SMILES: O=C(c1cnc2cncc(-c3ccc(C(F)(F)F)cc3)c2n1)N1CCS(=O)(=O)CC1]

In a 25 ml round-bottomed flask, (8-bromopyrido[3,4-b]pyrazin-2-yl)-(1,1-dioxo-1,4-thiazinan-4-yl)methanone (70 mg, 189 µmol), 4-(trifluoromethyl)phenylboronic acid (35.8 mg, 189 µmol) and cesium carbonate (67.6 mg, 207 µmol) were combined with dioxane (10 ml) and water (1.0 ml) to give a light brown suspension. Bis(diphenylphosphino)ferrocene-palladium(II)dichloride (6.9 mg, 9.43 µmol) was added. The reaction mixture was heated at 80° C. for 2 hours. The crude reaction mixture was concentrated in vacuo and purified by chromatography (silica gel, ethyl acetate/heptane=20:80 to 100:0) to yield the title compound (60 mg, 73%) as light brown solid. MS: m/e=437.1 [M+H]$^+$.

Example 34

8-(4-Cyanophenyl)pyrido[4,3-b]pyrazine-2-carboxamide

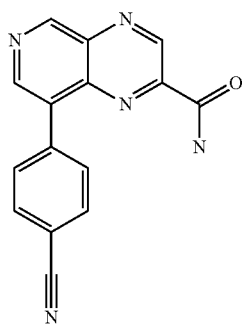 [SMILES: N#Cc1ccc(-c2cncc3ncc(C(N)=O)nc23)cc1]

In a 25 ml round-bottomed flask, 8-bromopyrido[4,3-b]pyrazine-2-carboxamide (50 mg, 198 µmol), 4-cyanophenylboronic acid (29.0 mg, 198 µmol) and cesium carbonate (129 mg, 395 µmol) were combined with dioxane (2.0 ml) and water (200 µl) to give a light brown solution. Bis(diphenylphosphino)ferrocene-palladium(II)dichloride (14.5 mg, 19.8 µmol) was added. The reaction mixture was heated at 80° C. for 30 minutes. The crude material was purified by chromatography (silica gel, ethyl acetate/heptane=20:80 to 100:0) to yield the title compound (19.4 mg, 36%) as light brown solid. MS: m/e=276.1 [M+H]$^+$.

Example 35

N-tert-Butyl-8-(4-(trifluoromethyl)phenyl)pyrido[4,3-b]pyrazine-2-carboxamide

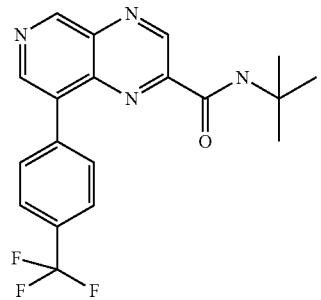

a) 8-Bromo-N-tert-butylpyrido[4,3-b]pyrazine-2-carboxamide

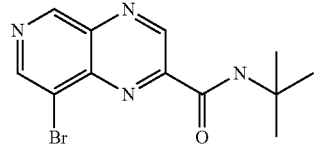 [SMILES: CC(C)(C)NC(=O)c1cnc2cncc(Br)c2n1]

In a 50 ml round-bottomed flask, 8-bromopyrido[4,3-b]pyrazine-2-carboxylic acid (200 mg, 787 µmol), 2-methylpropan-2-amine (57.6 mg, 82.7 µl, 787 µmol) and triethylamine (119 mg, 165 µl, 1.18 mmol) were combined with dimethylformamide (10 ml) to give a light brown suspension. Azabenzotriazol-1-yl)-N,N,N',N'-tetramethyluronium hexafluorophosphate (HATU, 329 mg, 866 µmol) was added and stirring was continued at room temperature. The crude reaction mixture was concentrated in vacuo and extracted with ethyl acetate/water. Chromatography (silica gel, ethyl acetate/heptane=20:80 to 100:0) yielded the title compound (156 mg, 64%) as white solid. MS: m/e=309.1, 311.1 [M+H]$^+$.

b) N-tert-Butyl-8-(4-(trifluoromethyl)phenyl)pyrido[4,3-b]pyrazine-2-carboxamide

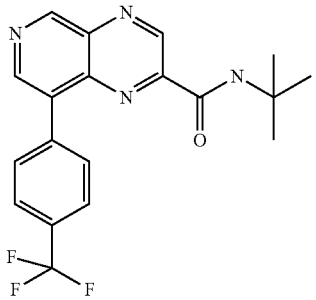

In a 25 ml round-bottomed flask, 8-bromo-N-tert-butylpyrido[4,3-b]pyrazine-2-carboxamide (50 mg, 162 µmol), 4-(trifluoromethyl)phenylboronic acid (30.7 mg, 162 µmol) and cesium carbonate (52.7 mg, 162 µmol) were combined with dioxane (10 ml) and water (1.0 ml) to give a light yellow solution. Bis(diphenylphosphino)ferrocene-palladium(II)dichloride (118 mg, 162 µmol) was added. The reaction mixture was heated at 80° C. for 2 hours. The crude reaction mixture was concentrated in vacuo and purified by chromatography (silica gel, ethyl acetate/heptane=20:80 to 100:0) to yield the title compound (50 mg, 83%) as off-white solid. MS: m/e=375.2 [M+H]+.

Example 36

8-(2,4-Dichlorophenyl)-N-(3-hydroxy-3-methylbutan-2-yl)pyrido[4,3-b]pyrazine-2-carboxamide

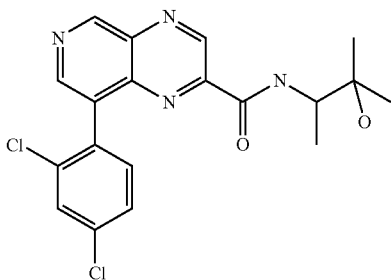 [SMILES: CC(NC(=O)c1cnc2cncc(-c3ccc(Cl)cc3Cl)c2n1)C(C)(C)O]

In a 25 ml round-bottomed flask, 8-bromo-N-(3-hydroxy-3-methylbutan-2-yl)pyrido[4,3-b]pyrazine-2-carboxamide (50 mg, 147 µmol), 2,4-dichlorophenylboronic acid (28.1 mg, 147 µmol) and cesium carbonate (52.8 mg, 162 µmol) were combined with dioxane (10.0 ml) and water (1.0 ml) to give a light brown suspension. Bis(diphenylphosphino)ferrocene-palladium(II)dichloride (5.39 mg, 7.37 µmol) was added. The reaction mixture was heated at 80° C. for 2 hours. The crude reaction mixture was concentrated in vacuo and purified by chromatography (silica gel, ethyl acetate/heptane=50:50 to 100:0) to yield the title compound (41 mg, 69%) as light brown solid. MS: m/e=405.6, 407.7 [M+H]+.

Example 37

8-(2-Chlorophenyl)-N-(3-hydroxy-3-methylbutan-2-yl)pyrido[4,3-b]pyrazine-2-carboxamide

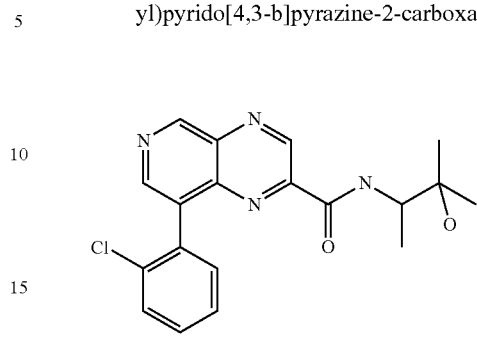

In a 25 ml round-bottomed flask, 8-bromo-N-(3-hydroxy-3-methylbutan-2-yl)pyrido[4,3-b]pyrazine-2-carboxamide (50 mg, 147 µmol), 2-chlorophenylboronic acid (23.1 mg, 147 µmol) and cesium carbonate (52.8 mg, 162 µmol) were combined with dioxane (10.0 ml) and water (1.0 ml) to give a light brown suspension. Bis(diphenylphosphino)ferrocene-palladium(II)dichloride (5.39 mg, 7.37 µmol) was added. The reaction mixture was heated at 80° C. for 2 hours. The crude reaction mixture was concentrated in vacuo and purified by chromatography (silica gel, ethyl acetate/heptane=50:50 to 100:0) to yield the title compound (50 mg, 92%) as off-white solid. MS: m/e=371.7 [M+H]+.

Example 38

(8-(4-Chloro-2-fluorophenyl)pyrido[4,3-b]pyrazin-2-yl)(3-hydroxypyrrolidin-1-yl)methanone

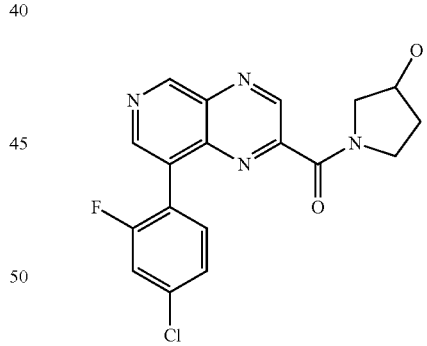

In a 25 ml round-bottomed flask, (8-bromopyrido[4,3-b]pyrazin-2-yl)(3-hydroxypyrrolidin-1-yl)methanone (35 mg, 108 µmol), 4-chloro-2-fluorophenylboronic acid (18.9 mg, 108 µmol) and cesium carbonate (38.8 mg, 119 µmol) were combined with dioxane (10 ml) and water (1.0 ml) to give a light brown solution. Bis(diphenylphosphino)ferrocene-palladium(II)dichloride (3.96 mg, 5.42 µmol) was added. The reaction mixture was heated at 90° C. for 4 hours. The crude material was concentrated in vacuo and purified by chromatography (silica gel, ethyl acetate/heptane=25:75 to 100:0) to yield the title compound (9.2 mg, 23%) as off-white solid. MS: m/e=373.2 [M+H]+.

Example 39

(8-(2,4-Dichlorophenyl)pyrido[4,3-b]pyrazin-2-yl)(3-hydroxypyrrolidin-1-yl)methanone

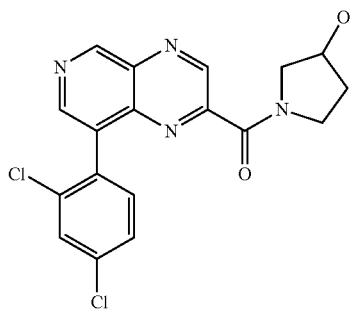 [SMILES: O=C(c1cnc2cncc(-c3ccc(Cl)cc3Cl)c2n1)N1CCC(O)C1]

In a 25 ml round-bottomed flask, (8-bromopyrido[4,3-b]pyrazin-2-yl)(3-hydroxypyrrolidin-1-yl)methanone (35 mg, 108 μmol), 2,4-dichlorophenylboronic acid (20.7 mg, 108 μmol) and cesium carbonate (38.8 mg, 119 μmol) were combined with dioxane (10 ml) and water (1.0 ml) to give a light brown solution. Bis(diphenylphosphino)ferrocene-palladium(II)dichloride (3.96 mg, 5.42 μmol) was added. The reaction mixture was heated at 90° C. for 4 hours. The crude material was concentrated in vacuo and purified by chromatography (silica gel, ethyl acetate/heptane=20:80 to 100:0) to yield the title compound (29 mg, 69%) as light brown solid. MS: m/e=389.2, 391.2 [M+H]$^+$.

Example 40

(8-(2-Fluoro-5-(trifluoromethyl)phenyl)pyrido[4,3-b]pyrazin-2-yl)(3-hydroxypyrrolidin-1-yl)methanone

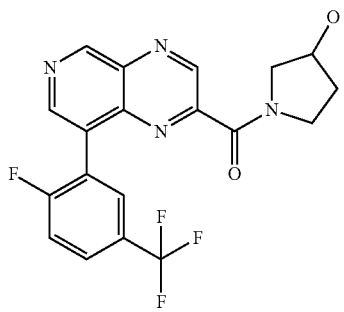 [SMILES: O=C(c1cnc2cncc(-c3cc(C(F)(F)F)ccc3F)c2n1)N1CCC(O)C1]

In a 25 ml round-bottomed flask, (8-bromopyrido[4,3-b]pyrazin-2-yl)(3-hydroxypyrrolidin-1-yl)methanone (35 mg, 108 μmol), 2-fluoro-5-(trifluoromethyl)phenylboronic acid (22.5 mg, 108 μmol) and cesium carbonate (70.6 mg, 217 μmol) were combined with dioxane (2.0 ml) and water (200 μl) to give a light brown suspension. Bis(diphenylphosphino)ferrocene-palladium(II)dichloride (7.93 mg, 10.8 μmol) was added. The reaction mixture was heated at 80° C. for 1 hour. The crude material was purified by chromatography (silica gel, ethyl acetate/heptane=20:80 to 100:0) to yield the title compound (20.1 mg, 46%) as colorless oil. MS: m/e=407.3 [M+H]$^+$.

Example 41

(3-Hydroxypyrrolidin-1-yl)(8-(3-(trifluoromethoxy)phenyl)pyrido[4,3-b]pyrazin-2-yl)methanone

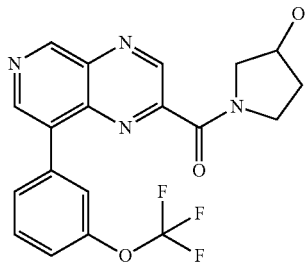 [SMILES: O=C(c1cnc2cncc(-c3cccc(OC(F)(F)F)c3)c2n1)N1CCC(O)C1]

In a 25 ml round-bottomed flask, (8-bromopyrido[4,3-b]pyrazin-2-yl)(3-hydroxypyrrolidin-1-yl)methanone (35 mg, 108 μmol), 3-(trifluoromethoxy)phenylboronic acid (22.3 mg, 108 μmol) and cesium carbonate (70.6 mg, 217 μmol) were combined with dioxane (2.0 ml) and water (200 μl) to give a light brown suspension. Bis(diphenylphosphino)ferrocene-palladium(II)dichloride (7.93 mg, 10.8 μmol) was added. The reaction mixture was heated at 80° C. for 1 hour. The crude material was purified by chromatography (silica gel, ethyl acetate/heptane=20:80 to 100:0) to yield the title compound (19.5 mg, 45%) as colorless oil. MS: m/e=405.3 [M+H]$^+$.

Example 42

8-(4,4-Difluoropiperidin-1-yl)pyrido[4,3-b]pyrazine-2-carboxamide

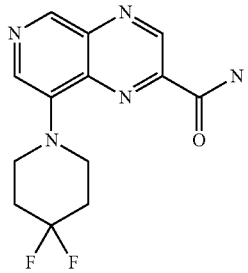

a) Methyl 8-bromopyrido[4,3-b]pyrazine-2-carboxylate

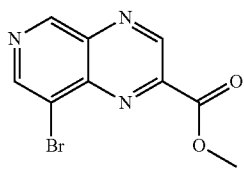

In a 50 ml round-bottomed flask, 8-bromopyrido[4,3-b]pyrazine-2-carboxylic acid (300 mg, 1.18 mmol) was combined with dichloromethane (10 ml) and 10 drops of dimethylformamide to give a light brown suspension. The mixture was cooled to 0° C. and oxalyl chloride (749 mg, 517 µl, 5.9 mmol) was added. The reaction mixture was stirred at 0° C. for 1 hour and then at room temperature for 1 hour. The mixture was concentrated in vacuo and dissolved in dichloromethane (10 ml). It was then slowly added to excess methanol at 0° C. After 1 hour of stirring the mixture was concentrated in vacuo to yield the title compound (148 mg, 47%) as off-white solid. MS: m/e=268.0, 270.0 [M+H]$^+$.

b) Methyl 8-(4,4-difluoropiperidin-1-yl)pyrido[4,3-b]pyrazine-2-carboxylate

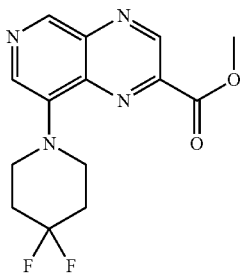

In a 25 ml three-necked flask, methyl 8-bromopyrido[4,3-b]pyrazine-2-carboxylate (100 mg, 373 µmol) and cesium carbonate (365 mg, 1.12 mmol) were combined with toluene (6.0 ml) to give a light brown suspension. Palladium(II) acetate (8.38 mg, 37.3 µmol) and 2,2'-bis(diphenylphosphino)-1,1'-binaphthyl (BINAP, 46.5 mg, 74.6 µmol) and 4,4-difluoropiperidine (45.2 mg, 373 µmol) were added. The reaction mixture was heated at 80° C. for 5 hours. The crude reaction mixture was concentrated in vacuo and purified by chromatography (silica gel, ethyl acetate/heptane=20:80 to 100:0) to yield the title compound (82 mg, 71%) as light red solid. MS: m/e=309.2 [M+H]$^+$.

c) 8-(4,4-Difluoropiperidin-1-yl)pyrido[4,3-b]pyrazine-2-carboxylic acid

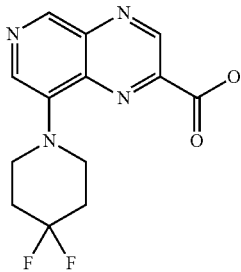 [SMILES: NC(=O)c1cnc2cncc(N3CCC(F)(F)CC3)c2n1]

In a 25 ml round-bottomed flask, methyl 8-(4,4-difluoropiperidin-1-yl)pyrido[4,3-b]pyrazine-2-carboxylate (80 mg, 260 µmol) was combined with dioxane (5.0 ml) to give a light red solution. Lithium hydroxide (7.46 mg, 311 µmol) in water (1.0 ml) was added and the mixture was stirred at room temperature overnight. The reaction mixture was poured into 5 ml water, acidified with aqueous hydrochloric acid (2N) and extracted with ethyl acetate (5×25 ml). The organic layers were dried over magnesium sulfate, concentrated and dried in vacuo to yield the title compound (79 mg, 93%) as light red solid. MS: m/e=293.3 [M–H]$^-$.

d) 8-(4,4-Difluoropiperidin-1-yl)pyrido[4,3-b]pyrazine-2-carboxamide

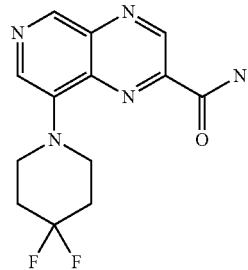 [SMILES: NC(=O)c1cnc2cncc(N3CCC(F)(F)CC3)c2n1]

In a 25 ml round-bottomed flask, 8-(4,4-difluoropiperidin-1-yl)pyrido[4,3-b]pyrazine-2-carboxylic acid (70 mg, 238 µmol) was combined with dichloromethane (5.0 ml) and 3 drops of dimethylformamide to give a red suspension. The mixture was cooled to 0° C. and then oxalyl chloride (302 mg, 208 µl, 2.38 mmol) was added slowly. The reaction mixture was stirred at 0° C. for 20 minutes and then for 30 minutes at room temperature. The mixture was concentrated in vacuo, taken up in dichloromethane (5.0 ml) and added to a mixture of triethylamine (72.2 mg, 99.5 µl, 714 µmol) and ammonium hydroxide (25% in water, 4.5 g, 5 ml, 128 mmol) at 0° C. The mixture was stirred overnight at room temperature. Extraction with dichlormethane/water and chromatography (silica gel, ethyl acetate/heptane=50:50 to 100:0) yielded the title compound (9 mg, 13%) as orange solid. MS: m/e=294.2 [M+H]$^+$.

Example 43

(8-(6-Chloropyridin-3-yl)pyrido[4,3-b]pyrazin-2-yl)(3-hydroxypyrrolidin-1-yl)methanone

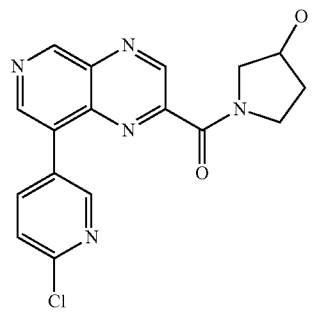

In a 25 ml round-bottomed flask, (8-bromopyrido[4,3-b]pyrazin-2-yl)(3-hydroxypyrrolidin-1-yl)methanone (35 mg, 108 µmol), 6-chloropyridin-3-ylboronic acid (17.0 mg, 108 µmol) and cesium carbonate (70.6 mg, 217 µmol) were combined with dioxane (2.0 ml) and water (200 µl) to give a light brown suspension. Bis(diphenylphosphino)ferrocene-palladium(II)dichloride (7.93 mg, 10.8 µmol) was added. The reaction mixture was heated at 80° C. for 1 hour. The crude material was purified by chromatography (silica gel, ethyl acetate/heptane=20:80 to 100:0) to yield the title compound (32 mg, 83%) as off-white solid. MS: m/e=356.2 [M+H]+.

Example 44

(8-(4-Chloro-3-fluorophenyl)pyrido[4,3-b]pyrazin-2-yl)(3-hydroxypyrrolidin-1-yl)methanone

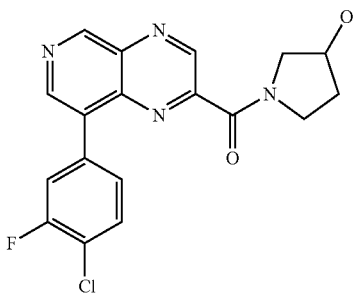 [SMILES: O=C(c1cnc2cncc(-c3ccc(Cl)c(F)c3)c2n1)N1CCC(O)C1]

In a 25 ml round-bottomed flask, (8-bromopyrido[4,3-b]pyrazin-2-yl)(3-hydroxypyrrolidin-1-yl)methanone (35 mg, 108 µmol), 4-chloro-3-fluorophenylboronic acid (18.9 mg, 108 µmol) and cesium carbonate (38.8 mg, 119 µmol) were combined with dioxane (10.0 ml) and water (0.5 ml) to give a light brown suspension. Bis(diphenylphosphino)ferrocene-palladium(II)dichloride (3.96 mg, 5.42 µmol) was added. The reaction mixture was heated at 90° C. for 1 hour. The crude material was concentrated in vacuo and purified by chromatography (silica gel, ethyl acetate/heptane=25:75 to 100:0) to yield the title compound (6 mg, 15%) as light brown solid. MS: m/e=373.2 [M+H]+.

Example 45

(8-(2-Fluoro-4-(trifluoromethyl)phenyl)pyrido[4,3-b]pyrazin-2-yl)(3-hydroxypyrrolidin-1-yl)methanone

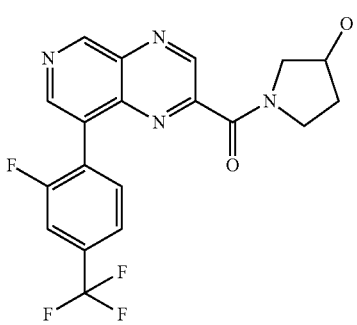 [SMILES: O=C(c1cnc2cncc(-c3ccc(C(F)(F)F)cc3F)c2n1)N1CCC(O)C1]

In a 25 ml round-bottomed flask, (8-bromopyrido[4,3-b]pyrazin-2-yl)(3-hydroxypyrrolidin-1-yl)methanone (35 mg, 108 µmol), 2-fluoro-4-(trifluoromethyl)phenylboronic acid (22.5 mg, 108 µmol) and cesium carbonate (70.6 mg, 217 µmol) were combined with dioxane (2.0 ml) and water (200 µl) to give a light brown suspension. Bis(diphenylphosphino)ferrocene-palladium(II)dichloride (7.93 mg, 10.8 µmol) was added. The reaction mixture was heated at 80° C. for 1 hour. The crude material was purified by chromatography (silica gel, ethyl acetate/heptane=20:80 to 100:0) to yield the title compound (11.2 mg, 25%) as off-white solid. MS: m/e=407.3 [M+H]+.

Example 46

8-(4-Chloro-3-fluorophenyl)-N-(3-hydroxy-3-methylbutan-2-yl)pyrido[4,3-b]pyrazine-2-carboxamide

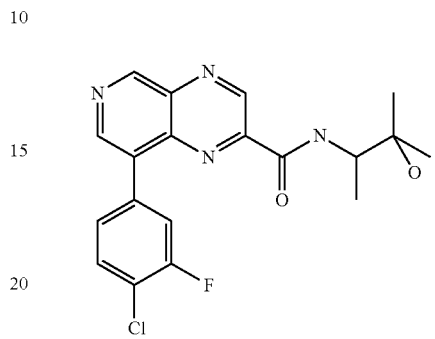

In a 25 ml round-bottomed flask, 8-bromo-N-(3-hydroxy-3-methylbutan-2-yl)pyrido[4,3-b]pyrazine-2-carboxamide (50 mg, 147 µmol), 4-chloro-3-fluorophenylboronic acid (25.7 mg, 147 µmol) and cesium carbonate (96.1 mg, 295 µmol) were combined with dioxane (10 ml) and water (1.0 ml) to give a light brown suspension. Bis(diphenylphosphino)ferrocene-palladium(II)dichloride (10.8 mg, 14.7 µmol) was added. The reaction mixture was heated at 80° C. for 1 hour. The crude reaction mixture was concentrated in vacuo and purified by chromatography (silica gel, ethyl acetate/heptane=20:80 to 100:0) to yield the title compound (34 mg, 59%) as off-white solid. MS: m/e=389.3 [M+H]+.

Example 47

N-(3-Hydroxy-3-methylbutan-2-yl)-8-(3,4,5-trifluorophenyl)pyrido[4,3-b]pyrazine-2-carboxamide

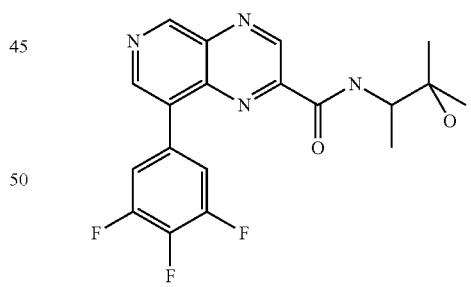

In a 25 ml round-bottomed flask, 8-bromo-N-(3-hydroxy-3-methylbutan-2-yl)pyrido[4,3-b]pyrazine-2-carboxamide (50 mg, 147 µmol), 3,4,5-trifluorophenylboronic acid (25.9 mg, 147 µmol) and cesium carbonate (96.1 mg, 295 µmol) were combined with dioxane (10 ml) and water (1.0 ml) to give a light brown suspension. Bis(diphenylphosphino)ferrocene-palladium(II)dichloride (10.8 mg, 14.7 µmol) was added. The reaction mixture was heated at 80° C. for 1 hour. The crude reaction mixture was concentrated in vacuo and purified by chromatography (silica gel, ethyl acetate/heptane=20:80 to 100:0) to yield the title compound (50 mg, 87%) as off-white solid. MS: m/e=391.2 [M+H]+.

Example 48

(8-(4-(Hydroxymethyl)phenyl)pyrido[4,3-b]pyrazin-2-yl)(3-hydroxypyrrolidin-1-yl)methanone

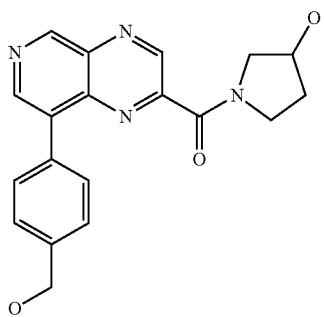 [SMILES: O=C(c1cnc2cncc(-c3ccc(CO)cc3)c2n1)N1CCC(O)C1]

In a 25 ml round-bottomed flask, (8-bromopyrido[4,3-b]pyrazin-2-yl)(3-hydroxypyrrolidin-1-yl)methanone (40 mg, 124 μmol), 4-(hydroxymethyl)phenylboronic acid (18.8 mg, 124 μmol) and cesium carbonate (44.4 mg, 136 μmol) were combined with dioxane (10 ml) and water (1.0 ml) to give a light brown suspension. Bis(diphenylphosphino)ferrocene-palladium(II)dichloride (4.53 mg, 6.19 μmol) was added. The reaction mixture was heated at 90° C. for 1 hour. The crude reaction mixture was concentrated in vacuo and purified by chromatography (silica gel, methanol/dichloromethane=2:98 to 7:93) to yield the title compound (30.6 mg, 71%) as brown solid. MS: m/e=351.2 [M+H]$^+$.

Example 49

N-(3-Hydroxy-3-methylbutan-2-yl)-8-(1-methyl-1H-pyrazol-5-yl)pyrido[4,3-b]pyrazine-2-carboxamide

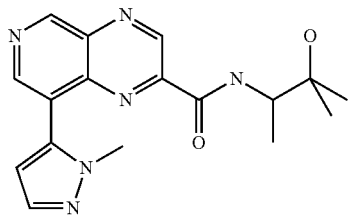 [SMILES: CC(NC(=O)c1cnc2cncc(-c3ccnn3C)c2n1)C(C)(C)O]

In a 25 ml round-bottomed flask, 8-bromo-N-(3-hydroxy-3-methylbutan-2-yl)pyrido[4,3-b]pyrazine-2-carboxamide (40 mg, 118 μmol), 1-methyl-5-(4,4,5,5-tetramethyl-1,3,2-dioxaborolan-2-yl)-1H-pyrazole (24.5 mg, 118 mol) and cesium carbonate (42.3 mg, 130 μmol) were combined with dioxane (10 ml) and water (1.0 ml) to give a light yellow suspension. Bis(diphenylphosphino)ferrocene-palladium(II)dichloride (4.31 mg, 5.9 mol) was added. The reaction mixture was heated at 90° C. overnight. The crude material was concentrated in vacuo and purified by chromatography (silica gel, ethyl acetate/heptane=20:80 to 100:0; then silica gel, methanol/dichloromethane=2:98 to 5:95) to yield the title compound (12.5 mg, 31%) as light grey solid. MS: m/e=341.2 [M+H]$^+$.

Example 50

8-(1-Methyl-1H-pyrazol-5-yl)pyrido[4,3-b]pyrazine-2-carboxamide

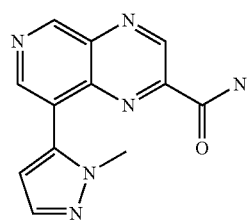

In a 25 ml round-bottomed flask, 8-bromopyrido[4,3-b]pyrazine-2-carboxamide (100 mg, 395 μmol), 1-methyl-5-(4,4,5,5-tetramethyl-1,3,2-dioxaborolan-2-yl)-1H-pyrazole (82.2 mg, 395 μmol) and cesium carbonate (258 mg, 790 μmol) were combined with dioxane (10.0 ml) and water (1.0 ml) to give a light brown solution. Bis(diphenylphosphino)ferrocene-palladium(II)dichloride (28.9 mg, 39.5 mol) was added. The reaction mixture was heated at 80° C. for 1 hour. The crude reaction mixture was concentrated in vacuo and purified by chromatography (silica gel, ethyl acetate/heptane=20:80 to 100:0) to yield the title compound (41 mg, 41%) as light grey solid. MS: m/e=255.2 [M+H]$^+$.

Example 51

N-(3-Hydroxy-3-methylbutan-2-yl)-8-(6-methylpyridin-3-yl)pyrido[4,3-b]pyrazine-2-carboxamide

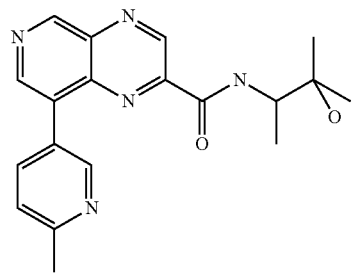 [SMILES: Cc1ccc(-c2cncc3ncc(C(=O)NC(C)C(C)(C)O)nc23)cn1]

In a 25 ml round-bottomed flask, 8-bromo-N-(3-hydroxy-3-methylbutan-2-yl)pyrido[4,3-b]pyrazine-2-carboxamide (50 mg, 147 μmol), 6-methylpyridin-3-ylboronic acid (20.2 mg, 147 μmol) and cesium carbonate (96.1 mg, 295 μmol) were combined with dioxane (10.0 ml) and water (1.0 ml) to give a light brown solution. Bis(diphenylphosphino)ferrocene-palladium(II)dichloride (10.8 mg, 14.7 μmol) was added. The reaction mixture was heated at 80° C. for 1 hour. The crude reaction mixture was concentrated in vacuo and purified by chromatography (silica gel, ethyl acetate/heptane=20:80 to 100:0) to yield the title compound (16 mg, 31%) as light brown solid. MS: m/e=352.3 [M+H]$^+$.

Example 52

(8-(3-Fluoro-4-(trifluoromethyl)phenyl)pyrido[4,3-b]pyrazin-2-yl)(3-hydroxypyrrolidin-1-yl)methanone

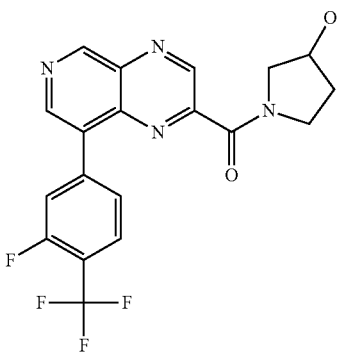 [SMILES: O=C(c1cnc2cncc(-c3ccc(C(F)(F)F)c(F)c3)c2n1)N1CCC(O)C1]

In a 25 ml round-bottomed flask, (8-bromopyrido[4,3-b]pyrazin-2-yl)(3-hydroxypyrrolidin-1-yl)methanone (40 mg, 124 µmol), 3-fluoro-4-(trifluoromethyl)phenylboronic acid (25.7 mg, 124 µmol) and cesium carbonate (44.4 mg, 136 µmol) were combined with dioxane (10 ml) and water (1.0 ml) to give a light brown suspension. Bis(diphenylphosphino)ferrocene-palladium(II)dichloride (4.53 mg, 6.19 µmol) was added. The reaction mixture was heated at 90° C. for 1 hour. The crude reaction mixture was concentrated in vacuo and purified by chromatography (silica gel, methanol/dichloromethane=2:98 to 7:93) to yield the title compound (20.7 mg, 41%) as off-white solid. MS: m/e=407.3 [M+H]$^+$.

Example 53

N-(3-Hydroxy-3-methylbutan-2-yl)-8-(6-methylpyridin-2-yl)pyrido[4,3-b]pyrazine-2-carboxamide

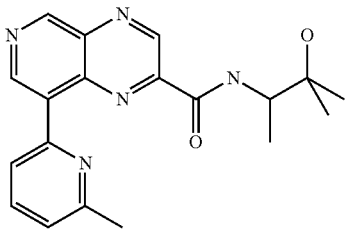

In a 25 ml round-bottomed flask, 8-bromo-N-(3-hydroxy-3-methylbutan-2-yl)pyrido[4,3-b]pyrazine-2-carboxamide (70 mg, 206 µmol), 6-methylpyridin-2-ylboronic acid (28.3 mg, 206 µmol) and cesium carbonate (74.0 mg, 227 µmol) were combined with dioxane (10 ml) and water (1.0 ml) to give a light yellow solution. Bis(diphenylphosphino)ferrocene-palladium(II)dichloride (7.55 mg, 10.3 µmol) was added. The reaction mixture was heated at 90° C. for 3 hours. Again, 6-methylpyridin-2-ylboronic acid (28.3 mg, 206 µmol) and cesium carbonate (74.0 mg, 227 µmol,) and bis(diphenylphosphino)ferrocene-palladium(II)dichloride (7.55 mg, 10.3 µmol) were added. The reaction mixture stirred over night at 90° C. A third time 6-methylpyridin-2-ylboronic acid (28.3 mg, 206 µmol) and cesium carbonate (74.0 mg, 227 µmol) and bis(diphenylphosphino)ferrocene-palladium(II)dichloride (7.55 mg, 10.3 µmol) were added. The reaction mixture was heated at 100° C. for 5 days. The crude material was concentrated in vacuo and purified by chromatography (silica gel, ethyl acetate/heptane=20:80 to 100:0) to yield the title compound (8.8 mg, 12%) as light grey solid. MS: m/e=352.3[M+H]$^+$.

We claim:
1. A compound of formula I

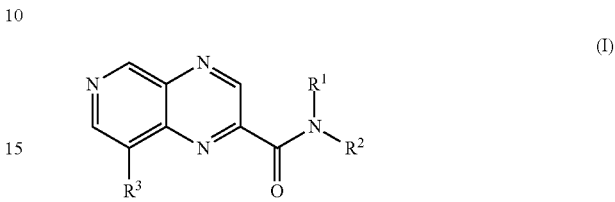

wherein
R$^1$ is hydrogen;
R$^2$ is hydrogen, lower alkyl, benzyl, lower alkyl substituted by hydroxy or cycloalkyl optionally substituted by cyano;
or R$^1$ and R$^2$ form together with the N-atom to which they are attached a heterocycloalkyl group, optionally containing an additional N, O or S ring atom, and which is optionally substituted by hydroxy;
R$^3$ is halogen,
phenyl optionally substituted by one or more halogen, cyano, lower alkyl substituted by halogen, lower alkoxy substituted by halogen, lower alkyl substituted by hydroxy, or is heteroaryl, optionally substituted by lower alkyl or halogen, or is 3,6-dihydropyran-4-yl, or is
piperidin-1-yl optionally substituted by one or more halogen;
or a pharmaceutically acceptable acid addition salt, to a racemic mixture or to it corresponding enantiomer and/or optical isomer thereof.

2. The compound according to claim 1, wherein R$^2$ is hydrogen, lower alkyl, benzyl lower alkyl substituted by hydroxy or cycloalkyl optionally substituted by cyano.

3. The compound according to claim 1 wherein the compound is selected form the group consisting of:
8-(4-chlorophenyl)pyrido[4,3-b]pyrazine-2-carboxamide;
8-(4-(trifluoromethyl)phenyl)pyrido[4,3-b]pyrazine-2-carboxamide;
8-bromo-N-(1-cyanocyclopropyl)pyrido[4,3-b]pyrazine-2-carboxamide;
8-(4-chlorophenyl)-N-(3-hydroxy-3-methylbutan-2-yl)pyrido[4,3-b]pyrazine-2-carboxamide;
N-(3-hydroxy-3-methylbutan-2-yl)-8-(4-(trifluoromethyl)phenyl)pyrido[4,3-b]pyrazine-2-carboxamide;
8-(4-chlorophenyl)-N-(1-cyanocyclopropyl)pyrido[4,3-b]pyrazine-2-carboxamide;
N-(1-cyanocyclopropyl)-8-(4-(trifluoromethyl)phenyl)pyrido[4,3-b]pyrazine-2-carboxamide;
N-benzyl-8-(4-(trifluoromethyl)phenyl)pyrido[4,3-b]pyrazine-2-carboxamide;
N-benzyl-8-(4-chlorophenyl)pyrido[4,3-b]pyrazine-2-carboxamide;
8-(2,4-dichlorophenyl)pyrido[4,3-b]pyrazine-2-carboxamide;
8-(4-fluorophenyl)pyrido[4,3-b]pyrazine-2-carboxamide;
8-(3,4,5-trifluorophenyl)pyrido[4,3-b]pyrazine-2-carboxamide;

8-(2-fluorophenyl)pyrido[4,3-b]pyrazine-2-carboxamide;
8-(2-fluoro-4-(trifluoromethyl)phenyl)pyrido[4,3-b]pyrazine-2-carboxamide;
8-(6-chloropyridin-3-yl)pyrido[4,3-b]pyrazine-2-carboxamide;
8-(4-(trifluoromethoxy)phenyl)pyrido[4,3-b]pyrazine-2-carboxamide;
8-(2-fluoro-5-(trifluoromethyl)phenyl)pyrido[4,3-b]pyrazine-2-carboxamide;
8-(3-(trifluoromethoxy)phenyl)pyrido[4,3-b]pyrazine-2-carboxamide;
8-(4-chloro-2-fluorophenyl)pyrido[4,3-b]pyrazine-2-carboxamide;
8-(4-chloro-3-fluorophenyl)pyrido[4,3-b]pyrazine-2-carboxamide;
8-(3-fluoro-4-(trifluoromethyl)phenyl)pyrido[4,3-b]pyrazine-2-carboxamide;
8-(3,6-dihydro-2H-pyran-4-yl)pyrido[4,3-b]pyrazine-2-carboxamide;
8-(3-(trifluoromethyl)phenyl)pyrido[4,3-b]pyrazine-2-carboxamide;
8-(3,4-difluorophenyl)pyrido[4,3-b]pyrazine-2-carboxamide;
8-(4-(hydroxymethyl)phenyl)pyrido[4,3-b]pyrazine-2-carboxamide;
N-benzyl-8-(pyridin-3-yl)pyrido[4,3-b]pyrazine-2-carboxamide;
8-(4-cyanophenyl)pyrido[4,3-b]pyrazine-2-carboxamide;
N-tert-butyl-8-(4-(trifluoromethyl)phenyl)pyrido[4,3-b]pyrazine-2-carboxamide;
8-(2,4-dichlorophenyl)-N-(3-hydroxy-3-methylbutan-2-yl)pyrido[4,3-b]pyrazine-2-carboxamide;
8-(2-chlorophenyl)-N-(3-hydroxy-3-methylbutan-2-yl)pyrido[4,3-b]pyrazine-2-carboxamide;
8-(4,4-difluoropiperidin-1-yl)pyrido[4,3-b]pyrazine-2-carboxamide;
8-(4-chloro-3-fluorophenyl)-N-(3-hydroxy-3-methylbutan-2-yl)pyrido[4,3-b]pyrazine-2-carboxamide;
N-(3-hydroxy-3-methylbutan-2-yl)-8-(3,4,5-trifluorophenyl)pyrido[4,3-b]pyrazine-2-carboxamide;
N-(3-hydroxy-3-methylbutan-2-yl)-8-(1-methyl-1H-pyrazol-5-yl)pyrido[4,3-b]pyrazine-2-carboxamide;
8-(1-methyl-1H-pyrazol-5-yl)pyrido[4,3-b]pyrazine-2-carboxamide;
N-(3-hydroxy-3-methylbutan-2-yl)-8-(6-methylpyridin-3-yl)pyrido[4,3-b]pyrazine-2-carboxamide; and,
N-(3-hydroxy-3-methylbutan-2-yl)-8-(6-methylpyridin-2-yl)pyrido[4,3-b]pyrazine-2-carboxamide; or, or a pharmaceutically acceptable acid addition salt, to a racemic mixture or to it corresponding enantiomer and/or optical isomer thereof.

4. The compound according to claim 1, wherein $R^1$ and $R^2$ form together with the N atom to which they are attached form a heterocycloalkyl group, optionally containing an additional N, O or S ring atom, and which is optionally substituted by hydroxyl.

5. The compound according to claim 4, wherein the compound is selected from the group consisting of:
(8-bromopyrido[4,3-b]pyrazin-2-yl)(morpholino)methanone;
(8-(4-chlorophenyl)pyrido[4,3-b]pyrazin-2-yl)(morpholino)methanone;
morpholino(8-(4-(trifluoromethyl)phenyl)pyrido[4,3-b]pyrazin-2-yl)methanone;
(3-hydroxypyrrolidin-1-yl)(8-(4-(trifluoromethyl)phenyl)pyrido[4,3-b]pyrazin-2-yl)methanone;
(8-(4-chlorophenyl)pyrido[4,3-b]pyrazin-2-yl)(3-hydroxypyrrolidin-1-yl)methanone;
[8-(4-chlorophenyl)pyrido[3,4-b]pyrazin-2-yl]-(1,1-dioxo-1,4-thiazinan-4-yl)methanone;
(1,1-dioxo-1,4-thiazinan-4-yl)-[8-[4-(trifluoromethyl)phenyl]pyrido[3,4-b]pyrazin-2-yl]methanone;
(8-(4-chloro-2-fluorophenyl)pyrido[4,3-b]pyrazin-2-yl)(3-hydroxypyrrolidin-1-yl)methanone;
8-(2,4-dichlorophenyl)pyrido[4,3-b]pyrazin-2-yl)(3-hydroxypyrrolidin-1-yl)methanone;
(8-(2-fluoro-5-(trifluoromethyl)phenyl)pyrido[4,3-b]pyrazin-2-yl)(3-hydroxypyrrolidin-1-yl)methanone;
(3-hydroxypyrrolidin-1-yl)(8-(3-(trifluoromethoxy)phenyl)pyrido[4,3-b]pyrazin-2-yl)methanone;
(8-(6-chloropyridin-3-yl)pyrido[4,3-b]pyrazin-2-yl)(3-hydroxypyrrolidin-1-yl)methanone;
(8-(4-chloro-3-fluorophenyl)pyrido[4,3-b]pyrazin-2-yl)(3-hydroxypyrrolidin-1-yl)methanone;
(8-(2-fluoro-4-(trifluoromethyl)phenyl)pyrido[4,3-b]pyrazin-2-yl)(3-hydroxypyrrolidin-1-yl)methanone;
(8-(4-(hydroxymethyl)phenyl)pyrido[4,3-b]pyrazin-2-yl)(3-hydroxypyrrolidin-1-yl)methanone; and,
(8-(3-fluoro-4-(trifluoromethyl)phenyl)pyrido[4,3-b]pyrazin-2-yl)(3-hydroxypyrrolidin-1-yl)methanone; or, or a pharmaceutically acceptable acid addition salt, to a racemic mixture or to it corresponding enantiomer and/or optical isomer thereof.

6. A process for the manufacture of a compound according to claim 1 which process comprises:
a) reacting a compound of formula

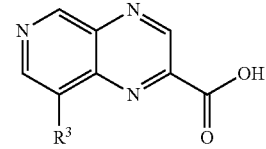

4 with a compound of formula $NHR^1R^2$ to afford a compound of formula (I)

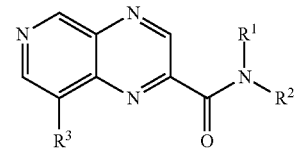

(I)

and, if desired, converting the compounds obtained into pharmaceutically acceptable acid addition salts; or,
b) reacting a compound of formula I-1

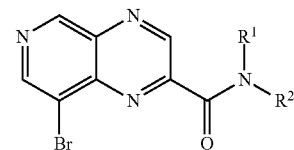

1-1 with a compound of formula $(HO)_2BR^3$ (3) to afford a compound of formula I

I

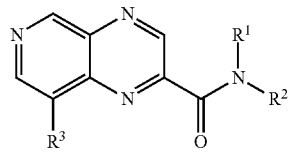

(I)

and, if desired, converting the compounds obtained into pharmaceutically acceptable acid addition salts.

7. A pharmaceutical composition comprising a compound according to claim 1 and at least one pharmaceutically acceptable excipient.

8. A method for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, selected from alcohol, opiates, methamphetamine, phencyclidine and cocaine comprising administering to a patient in need thereof a therapeutically effective amount of a compound according to claim 1.

* * * * *